(12) United States Patent
O'Hare et al.

(10) Patent No.: US 12,351,761 B2
(45) Date of Patent: Jul. 8, 2025

(54) CATALYTIC PROCESS

(71) Applicant: OXFORD UNIVERSITY INNOVATION LIMITED, Oxford (GB)

(72) Inventors: Dermot O'Hare, Oxford (GB); Shik Chi Tsang, Oxford (GB); Jean-Charles Buffet, Oxford (GB); Haohong Duan, Oxford (GB); Titipong Issariyakul, Bangkok (TH)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 697 days.

(21) Appl. No.: 17/283,071

(22) PCT Filed: Oct. 8, 2019

(86) PCT No.: PCT/GB2019/052835
§ 371 (c)(1),
(2) Date: Apr. 6, 2021

(87) PCT Pub. No.: WO2020/074870
PCT Pub. Date: Apr. 16, 2020

(65) Prior Publication Data
US 2021/0371754 A1 Dec. 2, 2021

(30) Foreign Application Priority Data
Oct. 11, 2018 (EP) ..................... 18199977

(51) Int. Cl.
*C10G 3/00* (2006.01)
*B01J 21/06* (2006.01)
*B01J 23/46* (2006.01)
*C07C 1/22* (2006.01)

(52) U.S. Cl.
CPC .............. *C10G 3/47* (2013.01); *B01J 21/063* (2013.01); *B01J 23/46* (2013.01); *C07C 1/22* (2013.01); *C07C 2521/06* (2013.01); *C07C 2523/46* (2013.01); *C10G 2300/70* (2013.01)

(58) Field of Classification Search
CPC .................. C10G 3/47; C10G 2300/70; C10G 2300/1014; C10G 3/50; C10G 3/44; B01J 21/063; B01J 23/46; C07C 1/22; C07C 2521/06; C07C 2523/46; Y02P 30/20
See application file for complete search history.

(56) References Cited

FOREIGN PATENT DOCUMENTS

EP 1795576 A1 6/2007

OTHER PUBLICATIONS

Furimsky, Catalytic hydrodeoxygenation. Applied Catalysis A: General. Jun. 12, 2000;199:147-190.
(Continued)

*Primary Examiner* — Thuan D Dang
(74) *Attorney, Agent, or Firm* — McCarter & English, LLP; Steven G. Davis; Wei Song

(57) ABSTRACT

A catalytic process for the deoxygenation of an organic substrate, such as a biomass or bio-oil, is described. The catalytic process is conducted in the presence of a gaseous mixture containing both hydrogen and nitrogen. The presence of nitrogen in the gaseous mixture gives rise inter-aliato increased catalytic activity and/or increased selectivity for aromatic reaction products.

16 Claims, 22 Drawing Sheets

(56) References Cited

OTHER PUBLICATIONS

Maluangnont et al., Production of liquid fuel from palmitic acid over nanocrystalline CeO2-based catalysts with minimal use of H2. Catalysis Communications. Dec. 2014;102:123-126.
Newman et al., Effects of support identity and metal dispersion in supported ruthenium hydrodeoxygenation catalysts. Applied Catalysis A: General. May 5, 2014;477:64-74.
Wijayapala et al., Hydrodeoxygenation (HDO) of Bio-Oil Model Compounds with Synthesis Gas Using a Water Gas Shift Catalyst with a Mo/Co/K Catalyst. Handbook of Climate Change Mitigation and Adaptation. Springer Science+Business Media, New York, pp. 1-34, (2015).
Yenumala et al., Reaction mechanism and kinetic modeling for the hydrodeoxygenation of triglycerides over alumina supported nickel catalyst. Reaction Kinetics, Mechanisms and Catalysis. Nov. 1, 2016;120:109-128.
International Search Report and Written Opinion for Application No. PCT/GB2019/052835, dated Oct. 29, 2019, 11 pages.
European Office Action for Application No. 18199977.2, dated Mar. 15, 2019, 10 pages.
Aika et al., Activation of Nitrogen by Alkali Metal Promoted Transition Metal I. Ammonia Synthesis over Ruthenium Promoted by Alkali Metal. Journal of Catalysis. 1972;27:424-431.
Alias et al., Hydrogenolysis of Glycerol to Propanediols Over Nano-Ru/C Catalyst with Ionic Liquid Addition. Advanced Materials Research. 2011;173:49-54.
Anisimov et al., First-principles calculations of the electronic structure and spectra of strongly correlated systems: dynamical mean-field theory. J Phys: Condens Matter. 1997;9:7359-7367.
Bergem et al., Low temperature aqueous phase hydrogenation of the light oxygenate fraction of bio-oil over supported ruthenium catalysts. Green Chem. 2017;19:3252-3262.
Boonyasuwat et al., Conversion of Guaiacol over Supported Ru Catalysts. Catal Lett. 2013;143:783-791.
Cargnello et al., Control of metal nanocrystal size reveals metal-support interface role for ceria catalysts. Science. Aug. 16, 2013;341(6147):771-3.
Chang et al., The promotional role of water in heterogeneous catalysis: mechanism insights from computational modeling. WIREs Comput Mol Sci. 2016;6:679-693.
Chang et al., Theoretical Investigations of the Catalytic Role of Water in Propene Epoxidation on Gold Nanoclusters: A Hydroperoxyl-Mediated Pathway. Nano Res. 2011;4(1):131-142.
Chen et al., Interfacial electronic effects control the reaction selectivity of platinum catalysts. Nat Mater. May 2016;15(5):564-9.
Elmasides et al., XPS and FTIR Study of Ru/Al2O3 and Ru/TiO2 Catalysts: Reduction Characteristics and Interaction with Methane-Oxygen Mixture. J Phys Chem. 1999;103:5227-5239.
Erisman et al., How a century of ammonia synthesis changed the world. Nature Geoscience. Oct. 2008;1:636-639.
Gago et al., Correlation between bonding structure and microstructure in fullerenelike carbon nitride thin films. Physical Review B. 2005;71:125414, 6 pages.
Jahn, An improved method for the diimide hydrogenation of butadiene and isoprene containing polymers. Journal of Polymer Science Part A: Polymer Chemistry. Mar. 15, 1992;30(3):397-408.
Henkelman et al., A climbing image nudged elastic band method for finding saddle points and minimum energy paths. Journal of Chemical Physics. Dec. 8, 2000;113(22):9901-9904.
Honkala et al., Ammonia synthesis from first-principles calculations. Science. Jan. 28, 2005;307(5709):555-8.
Hori et al., Synthesis of Heterocycles Utilizing N2—TiCl4—Li-TMSCI. J Org Chem. 1995;60(6):1480-1481.
Jimenez et al., Spectroscopy of pi bonding in hard graphitic carbon nitride films: Superstructure of basal planes and hardening mechanisms. Physical Review B. Aug. 15, 2000;62(7):4261-4264.
Kebukawa et al., Exploring the Potential Formation of Organic Solids in Chondrites and Comets Through Polymerization of Interstellar Formaldehyde. The Astrophysical Journal. Jul. 1, 2013;771(19):1-12.
Kitano et al., Electride support boosts nitrogen dissociation over ruthenium catalyst and shifts the bottleneck in ammonia synthesis. Nat Commun. Mar. 30, 2015;6:6731, 9 pages.
Kresse et al., Efficient iterative schemes for ab initio total-energy calculations using a plane-wave basis set. Physical Review B. Oct. 15, 1996;54(16):169-186.
Kresse et al., From ultrasoft pseudopotentials to the projector augmented-wave method. Physical Review B. Jan. 15, 1999;59(3):1758-1775.
Kuga et al., Nitrogen isotopic fractionation during abiotic synthesis of organic solid particles. Earth and Planetary Science Letters. May 1, 2014;393:2-13, pre-publication edition.
Lee et al., Stabilizing cobalt catalysts for aqueous-phase reactions by strong metal-support interaction. Journal of Catalysis. 2015;330:19-27.
Li et al., Catalytic Transformation of Lignin for the Production of Chemicals and Fuels. Chem Rev. Nov. 11, 2015;115(21):11559-624.
Liu et al., Heterogeneous Fe3 single-cluster catalyst for ammonia synthesis via an associative mechanism. Nat Commun. Apr. 23, 2018;9(1):1610, 9 pages.
Luksirikul et al., Electron promotion by surface functional groups of single wall carbon nanotubes to overlying metal particles in a fuel-cell catalyst. Angew Chem Int Ed Engl. Jul. 9, 2012;51(28):6998-7001.
Ma et al., Surface Single-Cluster Catalyst for N2-to-NH3 Thermal Conversion. J Am Chem Soc. Jan. 10, 2018;140(1):46-49.
Mellmer et al., Solvent-enabled control of reactivity for liquid-phase reactions of biomass-derived compounds. Nature Catalysis. Mar. 2018;1:199-207.
Morgan, Resolving ruthenium: XPS studies of common ruthenium materials. Surf Interface Anal. 2015;47:1072-1079.
Nelson et al., Experimental and Theoretical Insights into the Hydrogen-Efficient Direct Hydrodeoxygenation Mechanism of Phenol over Ru/TiO2. ACS Catal. 2015;5:6509-6523.
Omotoso et al., Experimental and First-Principles Evidence for Interfacial Activity of Ru/TiO2 for the Direct Conversion of m-Cresol to Toluene. ChemCatChem. 2017;9:2642-2651.
Perdew et al., Generalized Gradient Approximation Made Simple. Phys Rev Lett. Oct. 28, 1996;77(18):3865-3868.
Schulz, Short history and present trends of Fischer-Tropsch synthesis. Applied Catalysis A: General. 1999:186:3-12.
Shaver et al., Activation of Molecular Nitrogen: Coordination, Cleavage and Functionalization of N2 Mediated By Metal Complexes. Adv Synth Catal. 2003;345:1062-1076.
Tang et al., On the Nature of Support Effects of Metal Dioxides MO2 (M = Ti, Zr, Hf, Ce, Th) in Single-Atom Gold Catalysts: Importance of Quantum Primogenic Effect. The Journal of Physical Chemistry C. 2016; 120:17514-17526.
Vol'Pin et al., Transformations of molecular nitrogen into aromatic amines under the action of titanium compounds. Inorganic Chimica Acta. Oct. 15, 1998;280(1-2):264-274.
Wei et al., Geometrical Structure of the Gold-Iron(III) Oxide Interfacial Perimeter for CO Oxidation. Angew Chem Int Ed Engl. Aug. 27, 2018;57(35):11289-11293.
Xu et al., Lignin depolymerisation strategies: towards valuable chemicals and fuels. Chem Soc Rev. Nov. 21, 2014;43(22):7485-500.
Zhang et al., Density Functional Theory Study on the Metal-Support Interaction between Ru Cluster and Anatase TiO2(101) Surface. The Journal of Physical Chemistry C. 2014;118:3514-3522.

CATALYTIC PROCESS

CROSS-REFERENCE TO RELATED APPLICATIONS

This application is a U.S. national stage filing, under 35 U.S.C. § 371 (c), of International Application No. PCT/GB2019/052835, filed on Oct. 8, 2019, which claims priority to European Patent Application No. 18199977.2, filed on Oct. 11, 2018. The entire contents of each of the aforementioned applications are incorporated herein by reference.

INTRODUCTION

The present invention relates to a catalytic process for the deoxygenation of an organic substrate, such as a biomass or bio-oil.

BACKGROUND OF THE INVENTION

Lignocellulosic biomass, consisting of complex structures of cellulose, hemicellulose and lignin, is expected to be one of the most promising renewable carbon sources for the production of hydrocarbon fuels and added-value chemicals.[1,2] Flash pyrolysis can be used to break highly energetic C—O—C and C—C chemical linkages in these structures, thus producing bio-oil as a platform material containing monomers and oligomers.[3] However, the resulting materials still contains a high oxygen content (up to 60 wt %), which needs to be reduced—termed upgrading—if the materials are to meet the extremely low levels required for use in fuels. Although, the pyrolysis process is economical, efficient and industrially-compatible[4], the upgrading process remains far from being commercially implementable, which hinders the ideal strategy of supplying fuels from renewable source.

The upgrading of bio-oil has been traditionally carried out via a catalytic hydrodeoxygenation (HDO) reaction using sulfided CoMo or NiMo catalysts.[5] However, sulfur loss is inevitable for these catalysts, which results in product contamination, and external sulfur compensation is required to mitigate deactivation. In addition, the reaction requires high temperature (approximately 300° C.) and $H_2$ pressure (20-100 bar), which presents economical and environmental concerns. Over the past decades, a variety of strategies have been developed to enhance HDO activity under milder conditions. One such strategy is to hydrogenate the $C_{aromatic}$—O bond to $C_{aliphatic}$—O, and to then deoxygenate (by dehydration) the resulting material using catalysts consisting of metal and solid acid.[6-8] Due to the reduced bond strength of $C_{aliphatic}$—O compared with $C_{aromatic}$—O,[9] the HDO reaction can be operated at lower temperatures (approximately <180° C.). However, the reaction mechanism results in total hydrogenation of $C_{aromatic}$=$C_{aromatic}$ bonds, which requires high $H_2$ consumption, and produces alkanes with low octane number.

Recently, another strategy is becoming more economically attractive, which is based on direct deoxygenation (DDO) of bio-oils. In this approach, the $C_{aromatic}$=$C_{aromatic}$ bonds remain largely intact, thereby allowing production of aromatics with high octane number, using a reduced concentration of $H_2$. However DDO at mild conditions remains challenging due to the bond strength of the $C_{aromatic}$—O bond (468 kJ/mol).[9]

In spite of the advances made by research in this field[10,11,12,13,14] there remains a need for improved processes for the catalytic deoxygenation of organic substrates, notably biomass or bio-oil organic substrates.

The present invention was devised with the foregoing in mind.

SUMMARY OF THE INVENTION

According to a first aspect of the present invention there is provided a catalytic process for reducing the oxygen content of an organic substrate, the process comprising the steps of:
a) providing a mixture comprising:
  i. the organic substrate, and
  ii. a catalyst;
b) contacting the mixture of step a) with a gaseous mixture comprising hydrogen gas and nitrogen gas,
wherein the volume ratio of hydrogen gas to nitrogen gas in step b) is 1:0.5 to 1:20.

According to a second aspect of the present invention there is provided a catalytic process for reducing the oxygen content of an organic substrate, the process comprising the steps of:
a) providing a mixture comprising:
  i. the organic substrate,
  ii. a solvent; and
  iii. a catalyst;
b) contacting the mixture of step a) with a gaseous mixture comprising hydrogen gas and nitrogen gas,
wherein the volume ratio of hydrogen gas to nitrogen gas in step b) is 1:0.5 to 1:20.

DETAILED DESCRIPTION OF THE INVENTION

Definitions

The term "alkyl" as used herein refers to straight or branched chain alkyl moieties, typically having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl (including neopentyl), hexyl and the like. In particular, an alkyl may have 1, 2, 3 or 4 carbon atoms.

The term "alkenyl" as used herein refers to straight or branched chain alkenyl moieties, typically having 2, 3, 4, 5 or 6 carbon atoms. The term includes reference to alkenyl moieties containing 1, 2 or 3 carbon-carbon double bonds (C=C). This term includes reference to groups such as ethenyl (vinyl), propenyl (allyl), butenyl, pentenyl and hexenyl, as well as both the cis and trans isomers thereof.

The term "alkoxy" as used herein refers to —O-alkyl moieties, wherein alkyl is straight or branched chain and comprises 1, 2, 3, 4, 5 or 6 carbon atoms. Alternatively, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

The terms "comprise", "comprises" and "comprising" used herein are synonymous with including but not limited to, meaning that they do not exclude the presence of other moieties, additives, components, integers or steps. Nevertheless, it will be understood that whenever such terms are used herein to describe an open-ended list of features, the skilled reader would necessarily infer that the corresponding closedlist of features—i.e. said list "consisting essentially of" or "consisting of" the specified features—is also being described.

Catalytic Process

In a first aspect, the present invention provides a catalytic process for reducing the oxygen content of an organic substrate, the process comprising the steps of:
a) providing a mixture comprising:
  i. the organic substrate, and
  ii. a catalyst;
b) contacting the mixture of step a) with a gaseous mixture comprising hydrogen gas and nitrogen gas, wherein the volume ratio of hydrogen gas to nitrogen gas in step b) is 1:0.5 to 1:20.

In a second aspect, the present invention provides a catalytic process for reducing the oxygen content of an organic substrate, the process comprising the steps of:
a) providing a mixture comprising:
  i. the organic substrate,
  ii. a solvent, and
  iii. a catalyst;
b) contacting the mixture of step a) with a gaseous mixture comprising hydrogen gas and nitrogen gas, wherein the volume ratio of hydrogen gas to nitrogen gas in step b) is 1:0.5 to 1:20.

The inventors have surprisingly found that the presence of nitrogen in step b) gives rise to a number of advantages. In particular, the inventors have demonstrated that the use of nitrogen in the gaseous mixture of step b) results in a marked improvement in catalytic activity, thereby resulting in an increased yield of deoxygenation products in a given period of time. Moreover, the inventors have illustrated that the presence of nitrogen in step b) gives rise to an increased selectivity towards high value aromatic (as opposed to aliphatic) reaction products. In addition, the use of nitrogen in step b) allows the deoxygenation process to be satisfactorily conducted at lower temperatures and pressures than would otherwise be required, thus presenting clear economic and/or environmental advantages. One or more of these improvements have been obtained using a number of different deoxygenation catalysts, thereby illustrating that the beneficial effect of nitrogen is not confined to any one particular catalyst.

Gas Composition

It will be appreciated that the amount of nitrogen gas used in the catalytic process of the invention is significantly greater than that which may be required to simply purge a reactor prior to carrying out a catalytic process.

In an embodiment, the volume ratio of hydrogen gas to nitrogen gas in step b) is 1:0.5 to 1:20. Suitably, the volume ratio of hydrogen gas to nitrogen gas in step b) is 1:0.5 to 1:10. More suitably, the volume ratio of hydrogen gas to nitrogen gas in step b) is 1:1 to 1:10. Even more suitably, the volume ratio of hydrogen gas to nitrogen gas in step b) is 1:2 to 1:10. Yet even more suitably, the volume ratio of hydrogen gas to nitrogen gas in step b) is 1:3 to 1:8. Most suitable, the volume ratio of hydrogen gas to nitrogen gas in step b) is 1:3.5 to 1:8.

In an embodiment, the volume ratio of hydrogen gas to nitrogen gas in step b) is 1:2.75 to 1:8.4 Suitably, the volume ratio of hydrogen gas to nitrogen gas in step b) is 1:2.75 to 1:6.5. More suitably, the volume ratio of hydrogen gas to nitrogen gas in step b) is 1:2.75 to 1:6.0. Even more suitably, the volume ratio of hydrogen gas to nitrogen gas in step b) is 1:2.75 to 1:5.5. Yet even more suitably, the volume ratio of hydrogen gas to nitrogen gas in step b) is 1:2.75 to 1:5.0. Yet even more suitably, the volume ratio of hydrogen gas to nitrogen gas in step b) is 1:2.75 to 1:4.5. Yet even more suitably, the volume ratio of hydrogen gas to nitrogen gas in step b) is 1:2.75 to 1:4.0. Most suitably, the volume ratio of hydrogen gas to nitrogen gas in step b) is 1:2.75 to 1:3.5.

In an embodiment, the volume ratio of hydrogen gas to nitrogen gas in step b) is 1:3.25 to 1:8.4 Suitably, the volume ratio of hydrogen gas to nitrogen gas in step b) is 1:3.25 to 1:6.5. More suitably, the volume ratio of hydrogen gas to nitrogen gas in step b) is 1:3.25 to 1:6.0. Even more suitably, the volume ratio of hydrogen gas to nitrogen gas in step b) is 1:3.25 to 1:5.5. Yet even more suitably, the volume ratio of hydrogen gas to nitrogen gas in step b) is 1:3.25 to 1:5.0. Yet even more suitably, the volume ratio of hydrogen gas to nitrogen gas in step b) is 1:3.25 to 1:4.5. Yet even more suitably, the volume ratio of hydrogen gas to nitrogen gas in step b) is 1:3.25 to 1:4.0. Most suitably, the volume ratio of hydrogen gas to nitrogen gas in step b) is 1:3.25 to 1:3.75.

In an embodiment, greater than 40 vol. % of the gaseous mixture used in step b) is composed of hydrogen and nitrogen. Suitably, greater than 50 vol. % of the gaseous mixture used in step b) is composed of hydrogen and nitrogen. More suitably, greater than 60 vol. % of the gaseous mixture used in step b) is composed of hydrogen and nitrogen. Even more suitably, greater than 70 vol. % of the gaseous mixture used in step b) is composed of hydrogen and nitrogen. Yet more suitably, greater than 80 vol. % of the gaseous mixture used in step b) is composed of hydrogen and nitrogen. Yet even more suitably, greater than 90 vol. % of the gaseous mixture used in step b) is composed of hydrogen and nitrogen.

Particularly suitably, the gaseous mixture consists essentially of, or consists of, hydrogen and nitrogen.

The gaseous mixture may contain one or more gases in addition to hydrogen and nitrogen. In an embodiment, the gaseous mixture further comprises helium gas.

In a particular embodiment, step b) is performed under 0.5-1.5 bar hydrogen and 0.5-6 bar $N_2$. Suitably, step b) is performed under 0.5-1.5 bar hydrogen and 1.5-5.5 bar $N_2$. More suitably, step b) is performed under 0.5-1.5 bar hydrogen and 2.0-5.0 bar $N_2$. Even more suitably, step b) is performed under 0.5-1.5 bar hydrogen and 2.0-4.5 bar $N_2$. Even more suitably, step b) is performed under 0.5-1.5 bar hydrogen and 2.5-4.0 bar $N_2$.

Catalyst

Any catalyst capable of catalysing the deoxygenation (e.g. hydrodeoxygenation or direct deoxygenation) of an organic substrate may be used in step a).

In an embodiment, the catalyst comprises one or more metals selected from the group consisting of Ru, Pt and Pd supported on a support material selected from the group consisting of titania, alumina, silica, zirconia and carbon. Suitably, the catalyst is selected from the group consisting of Ru/$TiO_2$, Ru/$SiO_2$, Pt/$TiO_2$, Pd/$TiO_2$ and Ru/C.

It will be appreciated by one of ordinary skill in the art that the catalyst used in the present process is present in a reduced form. The skilled person will be aware of various methods by which such reduced forms may be obtained, including but not limited to heating the pre-catalyst to a high temperature (e.g. 350-450° C.) under an atmosphere of $H_2$.

When the support material is $TiO_2$, the $TiO_2$ may be composed solely of anatase, solely of rutile, or of a mixture of anatase and rutile. Suitably, the $TiO_2$ comprises 60-100% by weight rutile and 0-40% by weight anatase. More suitably, the $TiO_2$ comprises 70-100% by weight rutile and 0-30% by weight anatase. Yet more suitably, the $TiO_2$ comprises 80-100% by weight rutile (e.g. 80-99.9% by weight) and 0-20% by weight anatase (e.g. 0.1-20% by weight).

When the support material is carbon, the carbon is suitably an activated carbon.

Particularly suitably, the catalyst is Ru/TiO$_2$. The skilled person will appreciate that Ru/TiO$_2$ (ruthenium titanate) can be prepared by a variety of techniques, including but not limited to a wet impregnation method, all of which are encompassed by the present process. Such techniques may include any number of additives and reagents, in addition to the ruthenium precursor and titania, whilst still yielding a ruthenium titanate catalyst. In particular, such techniques may employ the use of an ionic liquid (i.e. a salt (having a cation and an anion) in a liquid state), such as one comprising a dicyanamide anion and/or an imidazolium cation, examples of which include 1-ethyl-3-methylimidazolium dicyanamide, 1-butyl-3-methylimidazolium dicyanamide and 1-hexyl-3-methylimidazolium dicyanamide.

In an embodiment, the Ru/TiO$_2$ catalyst comprises 0.50-1.10 wt % of Ru. Suitably, the Ru/TiO$_2$ catalyst comprises 0.60-0.90 wt % of Ru. More suitably, the Ru/TiO$_2$ catalyst comprises 0.65-0.85 wt % of Ru.

In an embodiment, the average (mean) diameter of Ru particles in the Ru/TiO$_2$ catalyst, as determined by HAADF-STEM is 0.9-1.5 nm, suitably 1.05-1.35 nm.

Organic Substrate

In an embodiment, the organic substrate is one or more aromatic compounds.

In an embodiment, the organic substrate is one or more cyclic compounds.

In an embodiment, the organic substrate is one or more organic compounds, each having a molecular mass of ≤1000 g mol$^{-1}$. Suitably, the organic substrate is one or more organic compounds, each having a molecular mass of ≤750 g mol$^{-1}$. More suitably, the organic substrate is one or more organic compounds, each having a molecular mass of ≤500 g mol$^{-1}$. Most suitably, the organic substrate is one or more organic compounds, each having a molecular mass of ≤300 g mol$^{-1}$.

In an embodiment, the organic substrate is one or more organic compounds having a structure according to formula (I) or (II) shown below:

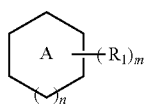

(I)

wherein
ring A is unsaturated, partially saturated or fully saturated, optionally containing 1 or 2 oxygen atoms within the ring;
n is a number selected from 0 and 1;
each R$_1$ is independently selected from (1-6C)alkyl, (2-6C)alkenyl, (2-6C)alkynyl, (1-6C)alkoxy, formyl, acyl, oxo, carboxy and hydroxyl; and
m is a number selected from 1, 2, 3, 4, 5 and 6,
providing that the compound contains at least one oxygen atom;

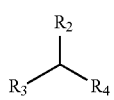

(II)

wherein
R$_2$ is oxo or hydroxyl; and
R$_3$ and R$_4$ are independently selected from (1-6C)alkyl, (2-6C)alkenyl, (2-6C)alkynyl, (1-6C)alkoxy, carboxy, oxo and hydroxyl, wherein any of said (1-6C)alkyl, (2-6C)alkenyl, (2-6C)alkynyl and (1-6C)alkoxy is optionally substituted with one or more groups selected from (1-6C)alkyl, (2-6C)alkenyl, (2-6C)alkynyl, (1-6C)alkoxy, formyl, acyl, oxo, carboxy and hydroxyl.

In an embodiment, ring A has a structure according to A1, A2, A3 or A4 shown below:

A1

A2

A3

A4

In an embodiment, m is a number selected from 1, 2, 3, 4 and 5. Suitably, m is a number selected from 1, 2, 3 or 4.

In an embodiment, each R$_1$ is independently selected from (1-4C)alkyl, (2-4C)alkenyl, (2-4C)alkynyl, (1-4C)alkoxy, formyl, acyl, oxo, carboxy and hydroxyl. Suitably, each R$_1$ is independently selected from hydroxy, (1-4C)alkoxy, (1-4C)alkyl and (2-4C)alkenyl. More suitably, at least one R$_1$ is selected from hydroxy and (1-2C)alkoxy.

In another embodiment, R$_2$ is oxo.

In another embodiment, R$_3$ and R$_4$ are independently selected from (1-4C)alkyl, (2-4C)alkenyl, (2-4C)alkynyl, (1-4C)alkoxy, carboxy, oxo and hydroxyl, wherein any of said (1-4C)alkyl, (2-4C)alkenyl, (2-4C)alkynyl and (1-4C) alkoxy is optionally substituted with one or more groups selected from (1-3C)alkyl, (2-3C)alkenyl, (2-3C)alkynyl, (1-3C)alkoxy, formyl, acyl, oxo, carboxy and hydroxyl.

In another embodiment, R$_3$ and R$_4$ are independently selected from (1-3C)alkyl, (2-3C)alkenyl, (1-3C)alkoxy, carboxy, oxo and hydroxyl, wherein any one of said (1-3C) alkyl, (2-3C)alkenyl and (1-3C)alkoxy is optionally substituted with one or more groups selected from (1-3C)alkyl, (2-3C)alkenyl, (1-3C)alkoxy, formyl, acyl, oxo, carboxy and hydroxyl.

In an embodiment, the organic substrate is one or more organic compounds having a structure according to formula (I) only.

In an embodiment, the organic substrate is not a fatty acid.

In an embodiment, the organic substrate is not a triglyceride.

In an embodiment, the organic substrate is neither a fatty acid nor a triglyceride.

In an embodiment, the organic substrate is a mixture of organic compounds comprising one or more selected from the group consisting of p-cresol, m-cresol, eugenol, guaiacol, 4-ethyl-guaiacol, 3-propyl-guaiacol, syringol, 4-methyl-syringol, 4-allyl-syringol and 1,3,5-trimethoxybenzene.

In an embodiment, the organic substrate is a mixture of organic compounds comprising p-cresol.

In an embodiment, the organic substrate is one or more organic compounds selected from the group consisting of p-cresol, m-cresol, eugenol, guaiacol, 4-ethyl-guaiacol, 3-propyl-guaiacol, syringol, 4-methyl-syringol, 4-allyl-syringol and 1,3,5-trimethoxybenzene.

In an embodiment, the organic substrate is a mixture of oxygen-containing compounds derived from plant matter (i.e. a plant-derived feedstock). Suitably, the mixture of oxygen-containing compounds derived from plant matter is a biomass or bio-oil. Suitably, the biomass or bio-oil is a liquid.

In a particular embodiment, the organic substrate is a liquid (e.g. a bio-oil) obtained by the pyrolysis of a plant-derived material (e.g. a biomass, such as lignocellulosic biomass).

In a particular embodiment, the organic substrate is a bio-oil. The bio-oil may be obtained (e.g. via pyrolysis) from a plant-derived material (e.g. a biomass, such as lignocellulosic biomass). The bio-oil may be liquid.

Particularly suitably, the organic substrate is pyrolised lignocellulosic biomass, which may be liquid.

Reaction Conditions

In an embodiment, step b) is carried out at a temperature of 40-500° C. Alternatively, step b) may be carried out at a temperature of 40-400° C. Alternatively still, step b) may be carried out at a temperature of 40-300° C. Alternatively still, step b) may be carried out at a temperature of 50-250° C. Alternatively still, step b) may be carried out at a temperature of 50-200° C. Alternatively still, step b) may be carried out at a temperature of 80-150° C. Alternatively still, step b) may be carried out at a temperature of 100-140° C.

Particularly suitably, step b) is carried out at a temperature of 40-250° C. More suitably, step b) is carried out at a temperature of 50-230° C. Even more suitably, step b) is carried out at a temperature of 80-220° C. Even more suitably, step b) is carried out at a temperature of 100-200° C. Most suitably, step b) is carried out at a temperature of 100-180° C.

Depending on the nature of the organic substrate, the mixture of step a) may further comprise a solvent. For example, if the organic substrate is a liquid at the conditions (e.g. temperature and pressure) under which the process is to be performed, a solvent may not be necessary. If, however, the organic substrate is such that it is a solid at the conditions (e.g. temperature and pressure) under which the process is to be performed, the mixture of step a) may further comprise a solvent.

Where the mixture of step a) comprises a solvent, any suitable solvent may be used. Suitably, the solvent is an organic solvent. For example, the solvent may be selected from decalin, octane, dodecane and mixtures thereof. Suitably, the solvent is decalin.

In a particular embodiment, when the mixture of step a) comprises a solvent, the solvent comprises less than 10 wt % water. Suitably, the solvent does not comprise water.

Step b) is suitably carried out under agitation (e.g. stirring).

In an embodiment, the process is performed in a batch or continuous manner. When the process is performed in a continuous manner, it may be conducted in a fixed bed reactor.

The following numbered statements 1-85 are not claims, but instead describe particular aspects and embodiments of the invention:

1. A catalytic process for reducing the oxygen content of an organic substrate, the process comprising the steps of:
   a) providing a mixture comprising:
      i. the organic substrate, and
      ii. a catalyst;
   b) contacting the mixture of step a) with a gaseous mixture comprising hydrogen gas and nitrogen gas, wherein the volume ratio of hydrogen gas to nitrogen gas in step b) is 1:0.5 to 1:20.
2. A catalytic process for reducing the oxygen content of an organic substrate, the process comprising the steps of:
   a) providing a mixture comprising:
      i. the organic substrate,
      ii. a solvent, and
      iii. a catalyst;
   b) contacting the mixture of step a) with a gaseous mixture comprising hydrogen gas and nitrogen gas, wherein the volume ratio of hydrogen gas to nitrogen gas in step b) is 1:0.5 to 1:20.
3. The process according to statement 1 or 2, wherein the volume ratio of hydrogen gas to nitrogen gas is 1:0.5 to 1:10.
4. The process according to statement 1 or 2, wherein the volume ratio of hydrogen gas to nitrogen gas is 1:1 to 1:10.
5. The process according to statement 1 or 2, wherein the volume ratio of hydrogen gas to nitrogen gas is 1:2 to 1:10.
6. The process according to statement 1 or 2, wherein the volume ratio of hydrogen gas to nitrogen gas is 1:3 to 1:8.
7. The process according to statement 1 or 2, wherein the volume ratio of hydrogen gas to nitrogen gas is 1:2.75 to 1:8.4.
8. The process according to statement 1 or 2, wherein the volume ratio of hydrogen gas to nitrogen gas is 1:2.75 to 1:6.5.
9. The process according to statement 1 or 2, wherein the volume ratio of hydrogen gas to nitrogen gas is 1:2.75 to 1:6.0.
10. The process according to statement 1 or 2, wherein the volume ratio of hydrogen gas to nitrogen gas is 1:2.75 to 1:5.5.
11. The process according to statement 1 or 2, wherein the volume ratio of hydrogen gas to nitrogen gas is 1:2.75 to 1:5.0.
12. The process according to statement 1 or 2, wherein the volume ratio of hydrogen gas to nitrogen gas is 1:2.75 to 1:4.5.
13. The process according to statement 1 or 2, wherein the volume ratio of hydrogen gas to nitrogen gas is 1:2.75 to 1:4.0.
14. The process according to statement 1 or 2, wherein the volume ratio of hydrogen gas to nitrogen gas is 1:2.75 to 1:3.5.
15. The process according to statement 1 or 2, wherein the volume ratio of hydrogen gas to nitrogen gas is 1:3.25 to 1:8.4.
16. The process according to statement 1 or 2, wherein the volume ratio of hydrogen gas to nitrogen gas is 1:3.25 to 1:6.5.

17. The process according to statement 1 or 2, wherein the volume ratio of hydrogen gas to nitrogen gas is 1:3.25 to 1:6.0.
18. The process according to statement 1 or 2, wherein the volume ratio of hydrogen gas to nitrogen gas is 1:3.25 to 1:5.5.
19. The process according to statement 1 or 2, wherein the volume ratio of hydrogen gas to nitrogen gas is 1:3.25 to 1:5.0.
20. The process according to statement 1 or 2, wherein the volume ratio of hydrogen gas to nitrogen gas is 1:3.25 to 1:4.5.
21. The process according to statement 1 or 2, wherein the volume ratio of hydrogen gas to nitrogen gas is 1:3.25 to 1:4.0.
22. The process according to statement 1 or 2, wherein the volume ratio of hydrogen gas to nitrogen gas is 1:3.25 to 1:3.75.
23. The process according to any preceding statement, wherein the gaseous mixture further comprises helium gas.
24. The process according to any preceding statement, wherein greater than 40 vol. % of the gaseous mixture used in step b) is composed of hydrogen and nitrogen.
25. The process according to any preceding statement, wherein greater than 60 vol. % of the gaseous mixture used in step b) is composed of hydrogen and nitrogen.
26. The process according to any preceding statement, wherein greater than 80 vol. % of the gaseous mixture used in step b) is composed of hydrogen and nitrogen.
27. The process according to any preceding statement, wherein the gaseous mixture used in step b) consists of hydrogen and nitrogen.
28. The process according to any preceding statement, wherein the catalyst comprises one or more metals selected from the group consisting of Ru, Pt and Pd supported on a support material selected from the group consisting of titania, alumina, silica, zirconia and carbon.
29. The process according to any preceding statement, wherein the catalyst is selected from the group consisting of $Ru/TiO_2$, $Pd/TiO_2$ and Ru/C.
30. The process according to any preceding statement, wherein the catalyst is $Ru/TiO_2$.
31. The process according to any preceding statement, wherein the $Ru/TiO_2$ catalyst comprises 0.50-1.10 wt % of Ru.
32. The process according to any preceding statement, wherein the $Ru/TiO_2$ catalyst comprises 0.60-0.90 wt % of Ru.
33. The process according to any preceding statement, wherein the $Ru/TiO_2$ catalyst comprises 0.65-0.85 wt % of Ru.
34. The process according to any preceding statement, wherein the average (mean) diameter of Ru particles in the $Ru/TiO_2$ catalyst, as determined by HAADF-STEM is 0.9-1.5 nm.
35. The process according to any preceding statement, wherein the average (mean) diameter of Ru particles in the $Ru/TiO_2$ catalyst, as determined by HAADF-STEM is 1.05-1.35 nm
36. The process according to any preceding statement, wherein the organic substrate is one or more aromatic compounds.
37. The process according to any preceding statement, wherein the organic substrate is one or more cyclic compounds.
38. The process according to any preceding statement, wherein the organic substrate is one or more organic compounds, each having a molecular mass of $\leq 1000$ g $mol^{-1}$.
39. The process according to any preceding statement, wherein the organic substrate is one or more organic compounds, each having a molecular mass of $\leq 750$ g $mol^{-1}$.
40. The process according to any preceding statement, wherein the organic substrate is one or more organic compounds, each having a molecular mass of $\leq 500$ g $mol^{-1}$.
41. The process according to any preceding statement, wherein the organic substrate is one or more organic compounds, each having a molecular mass of $\leq 300$ g $mol^{-1}$.
42. The process according to any preceding statement, wherein the organic substrate is one or more organic compounds having a structure according to formula (I) or (II) shown below:

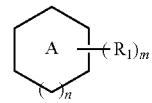

(I)

wherein
ring A is unsaturated, partially saturated or fully saturated, optionally containing 1 or 2 oxygen atoms within the ring;
n is a number selected from 0 and 1;
each $R_1$, is independently selected from (1-6C)alkyl, (2-6C)alkenyl, (2-6C)alkynyl, (1-6C)alkoxy, formyl, acyl, oxo, carboxy and hydroxyl; and
m is a number selected from 1, 2, 3, 4, 5 and 6,
providing that the compound contains at least one oxygen atom;

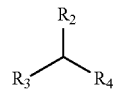

(II)

wherein
$R_2$ is oxo or hydroxyl; and
$R_3$ and $R_4$ are independently selected from (1-6C) alkyl, (2-6C)alkenyl, (2-6C)alkynyl, (1-6C) alkoxy, carboxy, oxo and hydroxyl, wherein any of said (1-6C)alkyl, (2-6C)alkenyl, (2-6C)alkynyl and (1-6C)alkoxy is optionally substituted with one or more groups selected from (1-6C)alkyl, (2-6C)alkenyl, (2-6C)alkynyl, (1-6C)alkoxy, formyl, acyl, oxo, carboxy and hydroxyl.
43. The process according to statement 42, wherein ring A has a structure according to A1, A2, A3 or A4 shown below:

A1

-continued

A2

A3

A4

44. The process according to statement 42 or 43, wherein m is a number selected from 1, 2, 3, 4 and 5.
45. The process according to statement 42, 43 or 44, wherein each $R_1$ is independently selected from (1-4C)alkyl, (2-4C)alkenyl, (2-4C)alkynyl, (1-4C)alkoxy, formyl, acyl, oxo, carboxy and hydroxyl.
46. The process according to any one of statements 42 to 45, wherein each $R_1$ is independently selected from hydroxy, (1-4C)alkoxy, (1-4C)alkyl and (2-4C)alkenyl.
47. The process according to any one of statements 42 to 46, wherein at least one $R_1$ is selected from hydroxy and (1-2C)alkoxy.
48. The process according to any one of statements 42 to 47, wherein $R_2$ is oxo.
49. The process according to any one of statements 42 to 48, wherein $R_3$ and $R_4$ are independently selected from (1-4C)alkyl, (2-4C)alkenyl, (2-4C)alkynyl, (1-4C)alkoxy, carboxy, oxo and hydroxyl, wherein any of said (1-4C)alkyl, (2-4C)alkenyl, (2-4C)alkynyl and (1-4C)alkoxy is optionally substituted with one or more groups selected from (1-3C)alkyl, (2-3C)alkenyl, (2-3C)alkynyl, (1-3C)alkoxy, formyl, acyl, oxo, carboxy and hydroxyl.
50. The process according to any one of statements 42 to 49, wherein $R_3$ and $R_4$ are independently selected from (1-3C)alkyl, (2-3C)alkenyl, (1-3C)alkoxy, carboxy, oxo and hydroxyl, wherein any one of said (1-3C)alkyl, (2-3C)alkenyl and (1-3C)alkoxy is optionally substituted with one or more groups selected from (1-3C)alkyl, (2-3C)alkenyl, (1-3C)alkoxy, formyl, acyl, oxo, carboxy and hydroxyl.
51. The process according to any preceding statement, the organic substrate is a mixture of organic compounds comprising one or more selected from the group consisting of p-cresol, m-cresol, eugenol, guaiacol, 4-ethyl-guaiacol, 3-propyl-guaiacol, syringol, 4-methyl-syringol, 4-allyl-syringol and 1,3,5-trimethoxybenzene.
52. The process according to any preceding statement, the organic substrate is a mixture of organic compounds comprising p-cresol.
53. The process according to any preceding statement, wherein the organic substrate is a mixture of oxygen-containing compounds derived from plant matter (i.e. a plant-derived feedstock).
54. The process according to statement 53, wherein the mixture of oxygen-containing compounds derived from plant matter is:
a biomass (e.g. lignocellulosic biomass),
a bio-oil, or
liquid obtainable by the pyrolysis of a plant-derived material.
55. The process according to any preceding statement, wherein the organic substrate is a bio-oil.
56. The process according to any preceding statement, wherein the organic substrate is pyrolised lignocellulosic biomass, which may be liquid.
57. The process according to any preceding statement, wherein step b) is carried out at a temperature of 40-500° C.
58. The process according to any preceding statement, wherein step b) is carried out at a temperature of 40-400° C.
59. The process according to any preceding statement, wherein step b) is carried out at a temperature of 40-300° C.
60. The process according to any preceding statement, wherein step b) is carried out at a temperature of 50-200° C.
61. The process according to any preceding statement, wherein step b) is carried out at a temperature of 80-150° C.
62. The process according to any preceding statement, wherein step b) is carried out at a temperature of 100-140° C.
63. The process according to any one of statements 1 to 56, wherein step b) is carried out at a temperature of 40-250° C.
64. The process according to any one of statements 1 to 56, wherein step b) is carried out at a temperature of 50-230° C.
65. The process according to any one of statements 1 to 56, wherein step b) is carried out at a temperature of 80-220° C.
66. The process according to any one of statements 1 to 56, wherein step b) is carried out at a temperature of 100-200° C.
67. The process according to any one of statements 1 to 56, wherein step b) is carried out at a temperature of 100-180° C.
68. The process according to any one of statements 2 to 67, wherein the solvent is an organic solvent.
69. The process according to statement 68, wherein the solvent is selected from decalin, octane, dodecane and mixtures thereof.
70. The process according to statement 69, wherein the solvent is decalin.
71. The process according to any preceding statement, wherein step b) is carried out under agitation (e.g. stirring).
72. The process according to any preceding statement, wherein the catalyst is $Ru/TiO_2$, and the volume ratio of hydrogen gas to nitrogen gas is 1:1 to 1:10.
73. The process according to any preceding statement, wherein
the catalyst is $Ru/TiO_2$,
the volume ratio of hydrogen gas to nitrogen gas is 1:1 to 1:10, and
the organic substrate is:
i) a mixture of oxygen-containing compounds derived from plant matter (i.e. a plant-derived feedstock),
ii) biomass, a bio-oil or a liquid obtainable by the pyrolysis of a plant-derived material,
iii) pyrolised lignocellulosic biomass, which may be liquid, or
iv) a mixture of oxygen-containing compounds comprising p-cresol.

74. The process according to any preceding statement, wherein
the catalyst is Ru/TiO$_2$, and
the volume ratio of hydrogen gas to nitrogen gas is 1:2.75 to 1:8.4.

75. The process according to any preceding statement, wherein
the catalyst is Ru/TiO$_2$,
the volume ratio of hydrogen gas to nitrogen gas is 1:2.75 to 1:8.4, and
the organic substrate is
i) a mixture of oxygen-containing compounds derived from plant matter (i.e. a plant-derived feedstock),
ii) biomass, a bio-oil or a liquid obtainable by the pyrolysis of a plant-derived material,
iii) pyrolised lignocellulosic biomass, which may be liquid, or
iv) a mixture of oxygen-containing compounds comprising p-cresol.

76. The process according to any preceding statement, wherein
the catalyst is Ru/TiO$_2$, and
the volume ratio of hydrogen gas to nitrogen gas is 1:3.25 to 1:8.4.

77. The process according to any preceding statement, wherein
the catalyst is Ru/TiO$_2$,
the volume ratio of hydrogen gas to nitrogen gas is 1:3.25 to 1:8.4, and
the organic substrate is:
i) a mixture of oxygen-containing compounds derived from plant matter (i.e. a plant-derived feedstock),
ii) biomass, a bio-oil or a liquid obtainable by the pyrolysis of a plant-derived material,
iii) pyrolysed lignocellulosic biomass, which may be liquid, or
iv) a mixture of oxygen-containing compounds comprising p-cresol.

78. The process according to any preceding statement, wherein
the catalyst is Ru/TiO$_2$, and
the Ru/TiO$_2$ catalyst comprises 0.50-1.10 wt % of Ru.

79. The process according to any preceding statement, wherein
the catalyst is Ru/TiO$_2$,
the Ru/TiO$_2$ catalyst comprises 0.50-1.10 wt % of Ru,
the volume ratio of hydrogen gas to nitrogen gas is 1:1 to 1:10, and
the organic substrate is
i) a mixture of oxygen-containing compounds derived from plant matter (i.e. a plant-derived feedstock),
ii) biomass, a bio-oil or a liquid obtainable by the pyrolysis of a plant-derived material,
iii) pyrolised lignocellulosic biomass, which may be liquid, or
iv) a mixture of oxygen-containing compounds comprising p-cresol.

80. The process according to any preceding statement, wherein
the catalyst comprises one or more metals selected from the group consisting of Ru, Pt and Pd supported on a support material selected from the group consisting of titania, alumina, silica and carbon, and
the volume ratio of hydrogen gas to nitrogen gas is 1:1 to 1:10.

81. The process according to any preceding statement, wherein
the catalyst comprises one or more metals selected from the group consisting of Ru, Pt and Pd supported on a support material selected from the group consisting of titania, alumina, silica and carbon,
the volume ratio of hydrogen gas to nitrogen gas is 1:1 to 1:10, and
the organic substrate is:
i) a mixture of oxygen-containing compounds derived from plant matter (i.e. a plant-derived feedstock),
ii) biomass, a bio-oil or a liquid obtainable by the pyrolysis of a plant-derived material,
iii) pyrolised lignocellulosic biomass, which may be liquid, or
iv) a mixture of oxygen-containing compounds comprising p-cresol.

82. The process according to any preceding statement, wherein
the catalyst comprises one or more metals selected from the group consisting of Ru, Pt and Pd supported on a support material selected from the group consisting of titania, alumina, silica and carbon, and
the volume ratio of hydrogen gas to nitrogen gas is 1:2.75 to 1:8.4.

83. The process according to any preceding statement, wherein
the catalyst comprises one or more metals selected from the group consisting of Ru, Pt and Pd supported on a support material selected from the group consisting of titania, alumina, silica and carbon,
the volume ratio of hydrogen gas to nitrogen gas is 1:2.75 to 1:8.4, and
the organic substrate is:
i) a mixture of oxygen-containing compounds derived from plant matter (i.e. a plant-derived feedstock),
ii) biomass, a bio-oil or a liquid obtainable by the pyrolysis of a plant-derived material,
iii) pyrolised lignocellulosic biomass, which may be liquid, or
iv) a mixture of oxygen-containing compounds comprising p-cresol.

84. The process according to any preceding statement, wherein
the catalyst comprises one or more metals selected from the group consisting of Ru, Pt and Pd supported on a support material selected from the group consisting of titania, alumina, silica and carbon, and
the volume ratio of hydrogen gas to nitrogen gas is 1:3.25 to 1:8.4.

85. The process according to any preceding statement, wherein
the catalyst comprises one or more metals selected from the group consisting of Ru, Pt and Pd supported on a support material selected from the group consisting of titania, alumina, silica and carbon,
the volume ratio of hydrogen gas to nitrogen gas is 1:3.25 to 1:8.4, and
the organic substrate is:
i) a mixture of oxygen-containing compounds derived from plant matter (i.e. a plant-derived feedstock), ii) biomass, a bio-oil or a liquid obtainable by the pyrolysis of a plant-derived material,
iii) pyrolised lignocellulosic biomass, which may be liquid, or
iv) a mixture of oxygen-containing compounds comprising p-cresol.

EXAMPLES

One or more examples of the invention will now be described, for the purpose of illustration only, with reference to the accompanying figures, in which:

FIG. 1 shows the effect of $N_2$ on the catalytic activity of various catalysts in the catalytic deoxygenation of p-cresol to toluene. Reaction conditions: p-cresol (0.195 mmol), decalin (8 mL), 120° C., 1 bar $H_2$ and 6 bar $N_2$ or 1 bar $H_2$ and 6 bar He, mixture stirred at 800 rpm. 10 mg of catalysts used. Ru/$TiO_2$, m-Ru/$TiO_2$ and Pd/$TiO_2$ contained 1.25 wt % metal. Ru/C, containing 5 wt. % Ru, was commercially-obtained.

FIG. 2 shows the effect of $N_2$ on the toluene selectively of various catalysts in the catalytic deoxygenation of p-cresol to toluene. Reaction conditions: p-cresol (0.195 mmol), decalin (8 mL), 120° C., 1 bar $H_2$ and 6 bar $N_2$ or 1 bar $H_2$ and 6 bar He, mixture stirred at 800 rpm. 10 mg of catalysts used. Ru/$TiO_2$, m-Ru/$TiO_2$ and Pd/$TiO_2$ contained 1.25 wt % metal. Ru/C, containing 5 wt. % Ru, was commercially-obtained.

FIG. 3 shows the $N_2$ pressure effect on the catalytic deoxygenation activity of p-cresol to toluene. Reaction conditions: p-cresol (0.195 mmol), m-Ru/$TiO_2$ (10 mg, including 1.25 wt % Ru), decalin (8 mL), 120° C., 6 bar He, 1 bar $H_2$ and 1-5 bar $N_2$, or 1 bar $H_2$ and 6 bar $N_2$, mixture stirred at 600 rpm.

FIG. 4 shows the $N_2$ pressure effect on the catalytic deoxygenation selectivity of p-cresol to toluene. Reaction conditions: p-cresol (0.195 mmol), m-Ru/$TiO_2$ (10 mg, including 1.25 wt % Ru), decalin (8 mL), 120° C., 6 bar He, 1 bar $H_2$ and 1-5 bar $N_2$, or 1 bar $H_2$ and 6 bar $N_2$, mixture stirred at 600 rpm.

FIG. 5 shows filtering gas effect (to avoid moisture and oxygen) on the catalytic deoxygenation activity of p-cresol to toluene. Reaction conditions: p-cresol (0.195 mmol), m-Ru/$TiO_2$ (10 mg, including 1.25 wt % Ru), decalin (8 mL), 120° C., 6 bar He and 1 bar $H_2$, or 6 bar $N_2$ and 1 bar, mixture stirred at 600 rpm.

FIG. 6 shows filtering gas effect (to avoid moisture and oxygen) on the toluene selectivity of deoxygenation of p-cresol to toluene. Reaction conditions: p-cresol (0.195 mmol), m-Ru/$TiO_2$ (10 mg, including 1.25 wt % Ru), decalin (8 mL), 120° C., 6 bar He and 1 bar $H_2$, or 6 bar $N_2$ and 1 bar, mixture stirred at 600 rpm.

Figure 9:
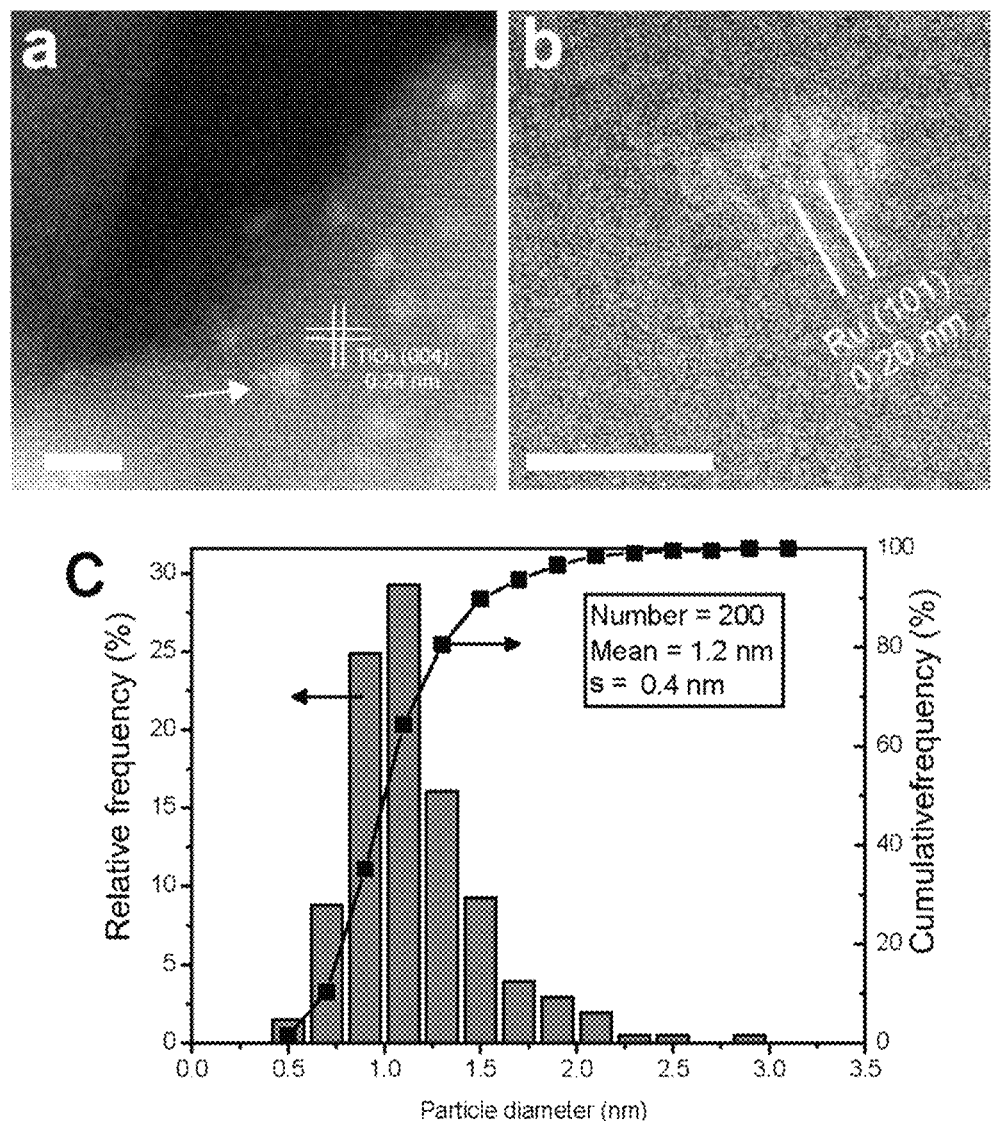
Figure 9:
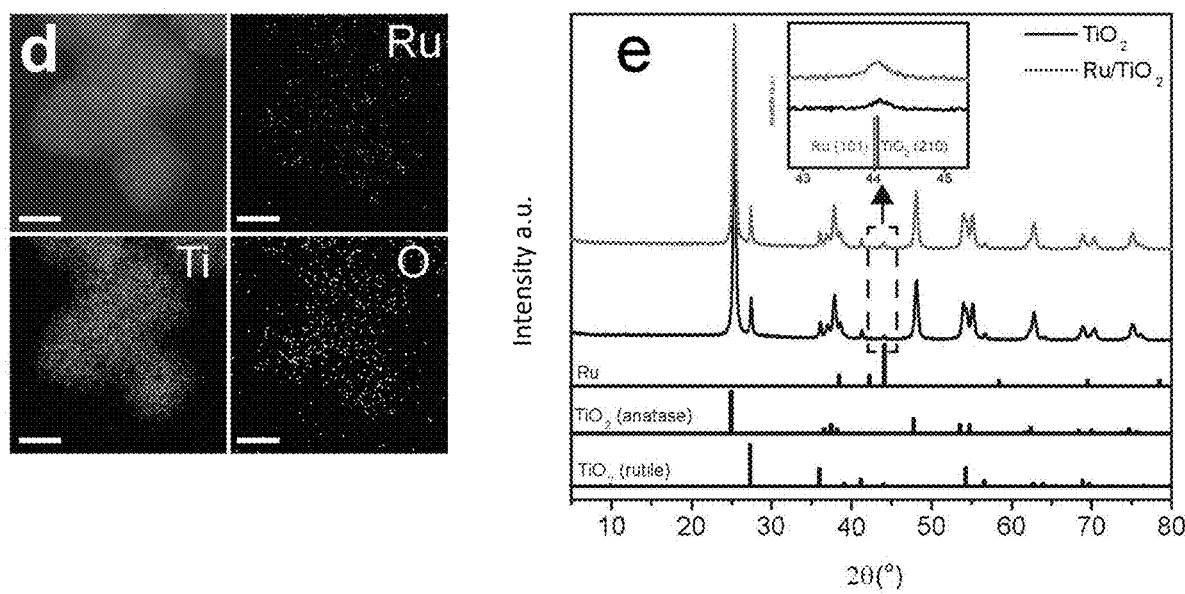

FIG. 9 shows structure characterisations of the Ru/$TiO_2$ catalyst. High-angle annular dark-field scanning transmission electron microscopy images of (a) a representative region and (b), an individual particle of the Ru/$TiO_2$ catalyst corresponding to the arrow in panel (a). Scale bar equals 2 nm in (a), and equals 1 nm in (b). (c), Size distribution of the Ru particles. (d), STEM-EDS elemental mapping results for Ru/$TiO_2$. Scale bars equal 10 nm. (e), X-ray diffraction patterns of Ru/$TiO_2$ catalyst and $TiO_2$. Inset highlights the reflection at around 2θ=44°.

Figure 10:
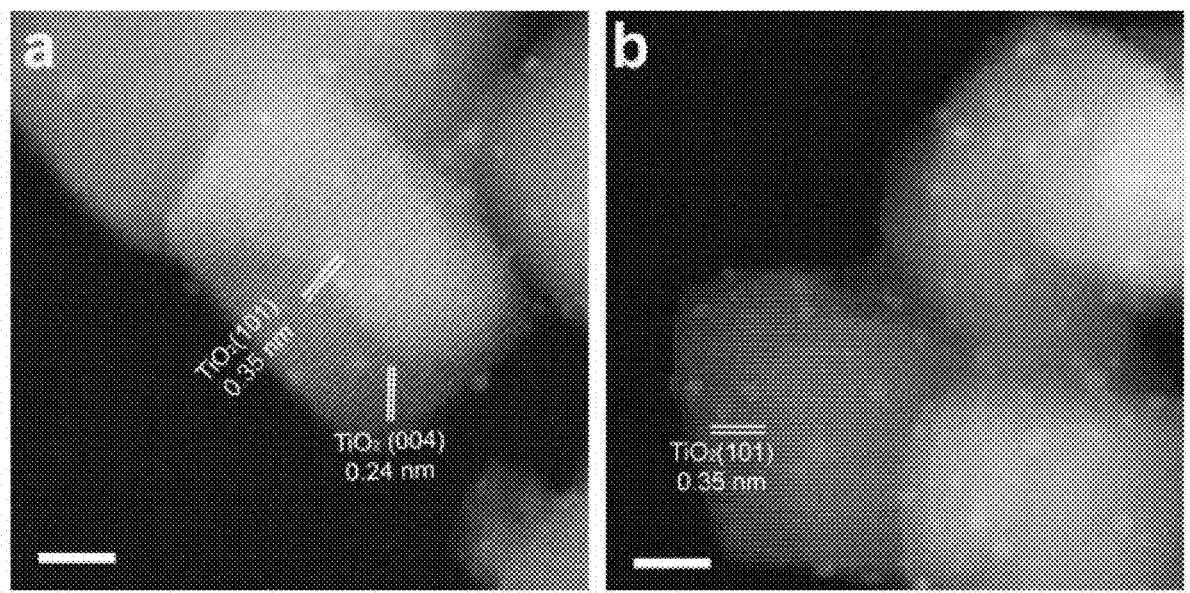

FIG. 10 shows representative HAADF images of Ru/$TiO_2$. Scale bars equal 5 nm.

Figure 11:
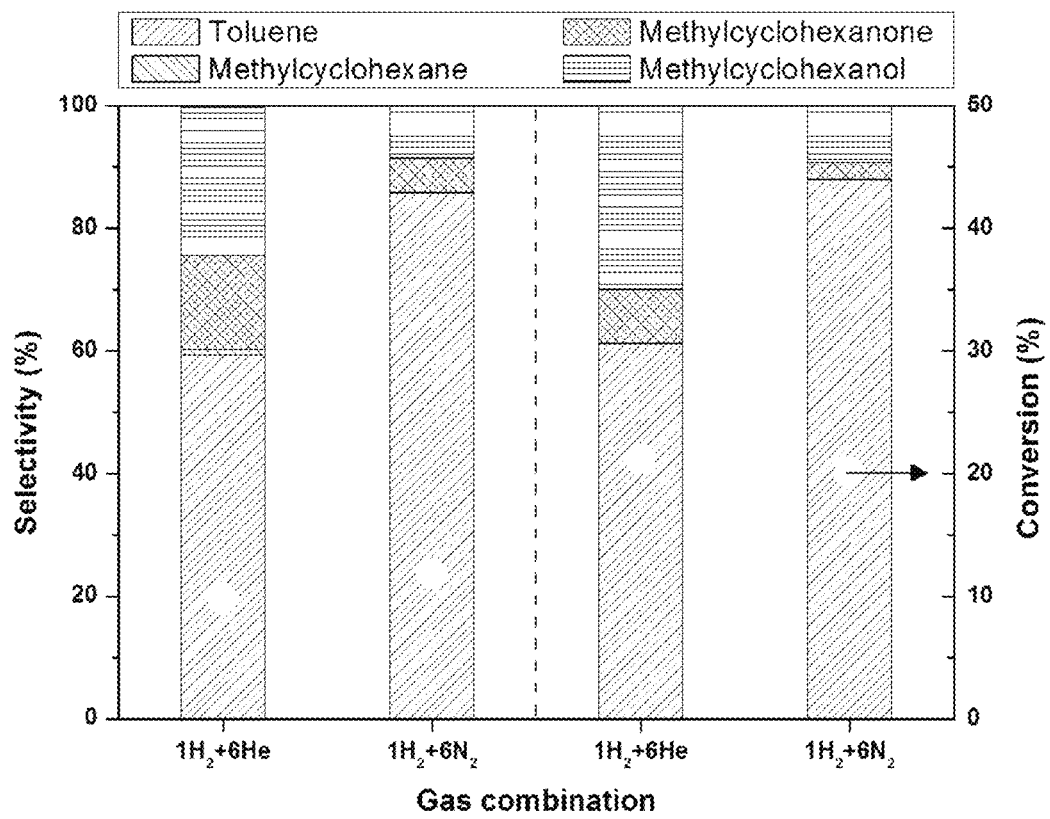
Figure 11:
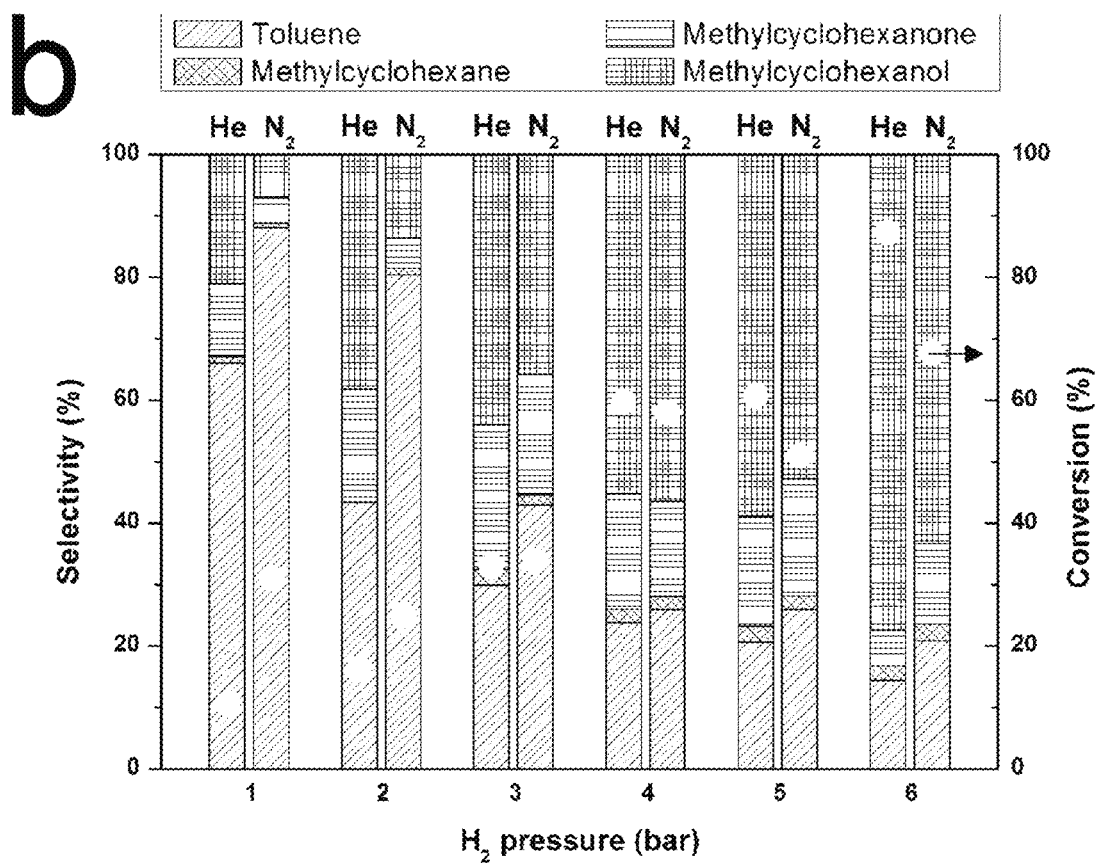
Figure 11:
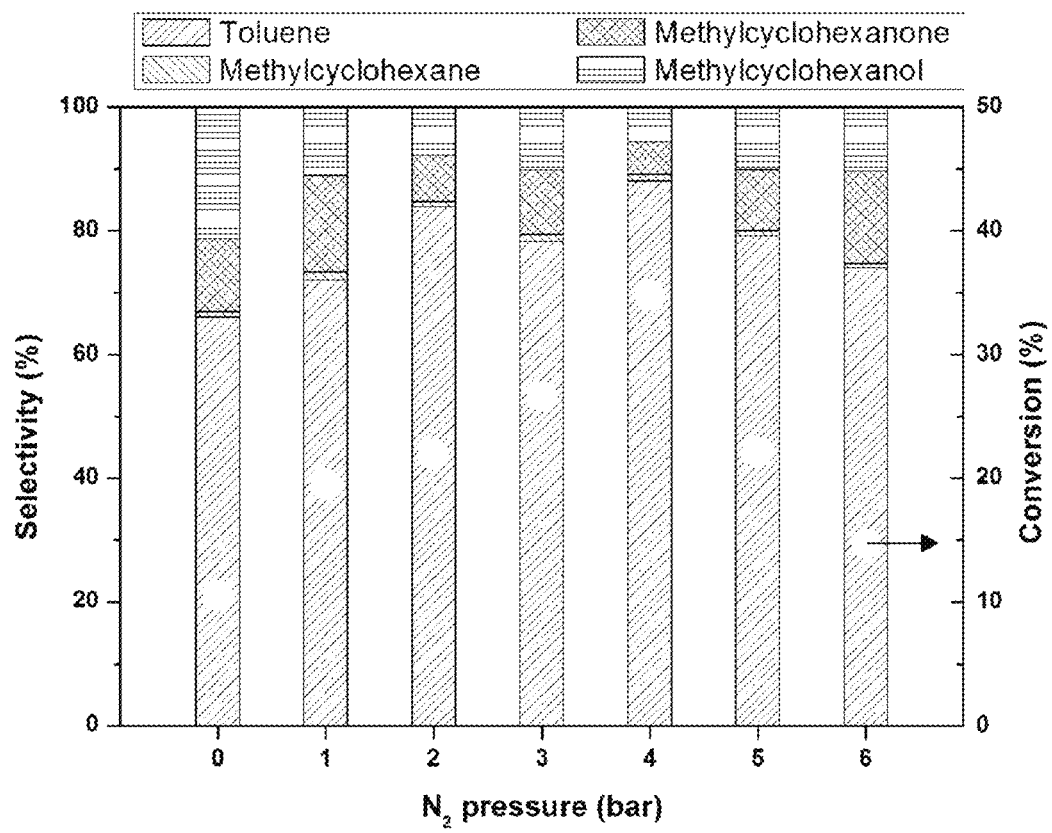
Figure 11:
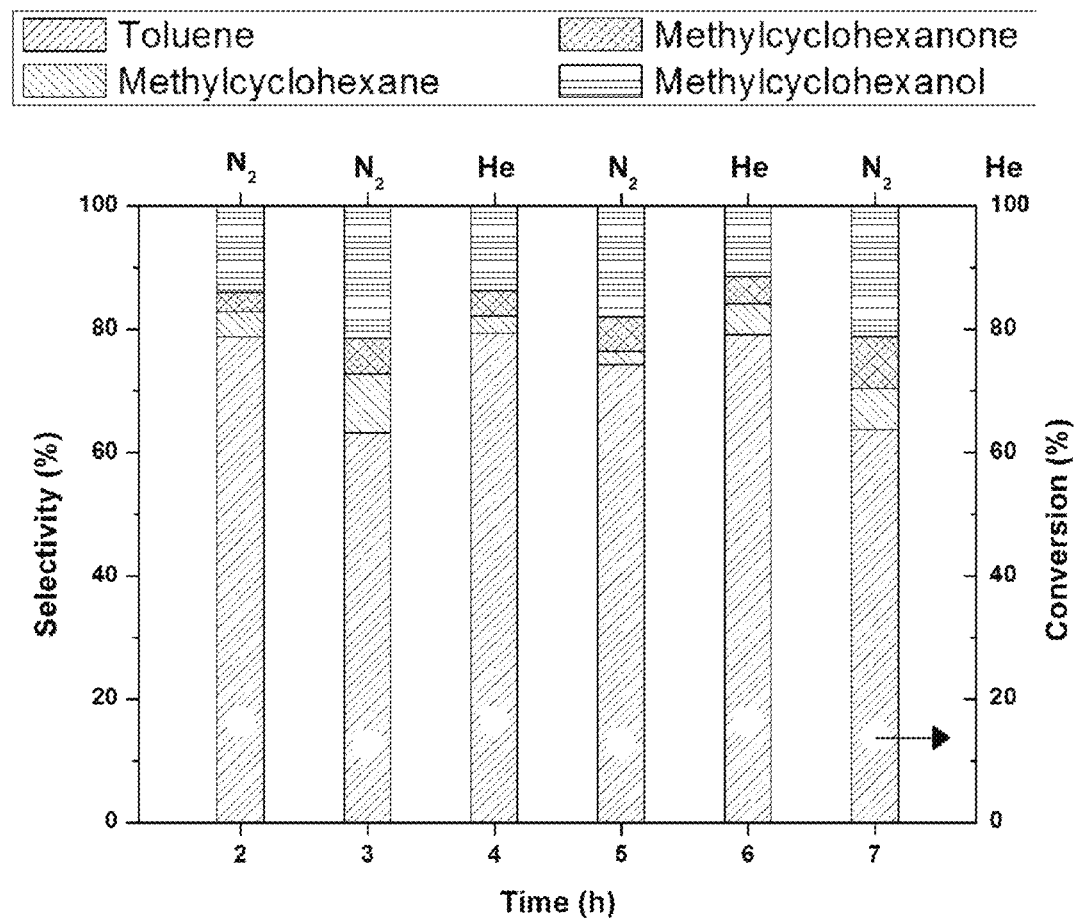

FIG. 11 shows catalytic performance promoted by $N_2$ in the hydrodeoxygenation of p-cresol using Ru/$TiO_2$ catalyst. Comparison of conversion and selectivity with or without $N_2$ in batch reaction. (a), Comparison at two different conversions, reaction conditions: (a), p-cresol (0.195 mmol), Ru/$TiO_2$ catalyst (25, 10, 25, 25 mg from left to right column), decalin (8 mL), 160° C., reaction time (1, 1, 4, 1 hour from the left to right column), system pressure of 1 bar $H_2$ and 6 bar He (or 1 bar $H_2$ and 6 bar $N_2$), mixture stirred at 600 rpm. (b), Comparison at varied $H_2$ pressures, reaction conditions: p-cresol (0.195 mmol), Ru/$TiO_2$ catalyst (25 mg), decalin (8 mL), 160° C., 1 hour, system pressure of 1-6 bar $H_2$ and 6 bar He (or 1-6 bar $H_2$ and 6 bar $N_2$), mixture stirred at 600 rpm. (c), Comparison at varied $N_2$ pressures, reaction conditions: p-cresol (0.195 mmol), Ru/$TiO_2$ catalyst (25 mg), decalin (8 mL), 160° C., 1 hour, system pressure of 1 bar $H_2$, 6 bar He and 0-6 bar $N_2$, mixture stirred at 600 rpm. (d), Comparison of conversion and selectivity with or without $N_2$ in fixed-bed reaction. Reaction conditions: p-cresol (concentration of 1.12 mg·$mL^{-1}$ with decalin as solvent, flow rate of 0.2 mL·$min^{-1}$), Ru/$TiO_2$ (100 mg), 180° C., system pressure of 1 bar $H_2$ and 6 bar He (or 1 bar $H_2$ and 6 bar $N_2$), $H_2$ flow rate of 5 $cm^3$(STP)$min^{-1}$, $N_2$ (or He) flow rate of 30 $cm^3$(STP)$min^{-1}$, weight hourly space velocity (WHSV, 0.134 $h^{-1}$).

Figure 12:
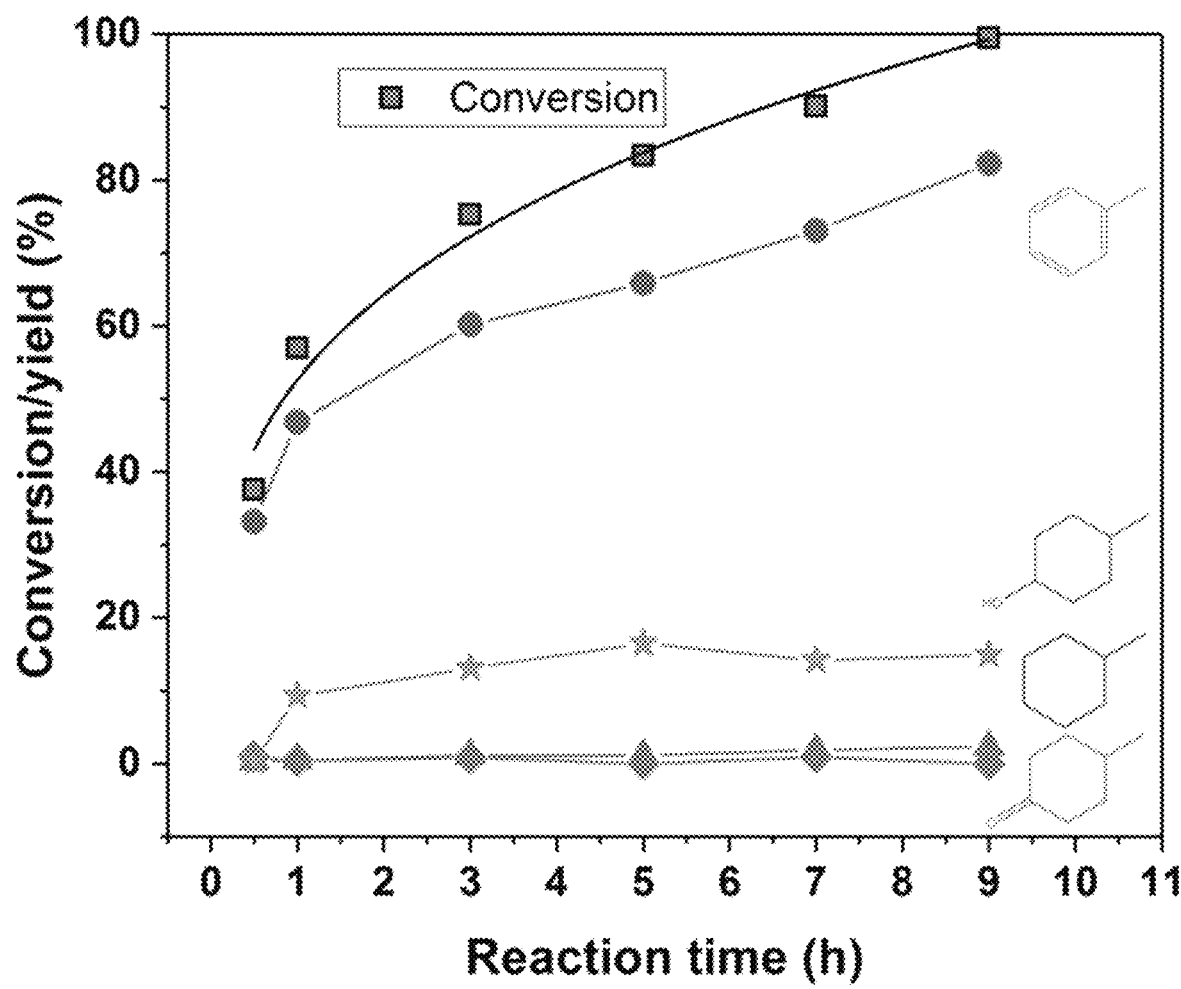

FIG. 12 shows time dependence of the p-cresol conversion and product yield. The reaction process by using Ru/$TiO_2$ catalyst in the presence of $N_2$ shows high toluene selectivity from the initial stage, and methylcyclohexanol or methylcyclohexene were not observed which are normally the reaction intermediates from the hydrodeoxygenation reaction following tandem reaction route[11]. Reaction conditions: batch reaction, p-cresol (0.195 mmol), Ru/$TiO_2$ (65 mg), decalin (8 mL), 160° C., reaction time from 0.5 to 9 hours, system pressure of 1 bar $H_2$ and 6 bar $N_2$, reaction mixture stirred at 600 rpm.

Figure 13:
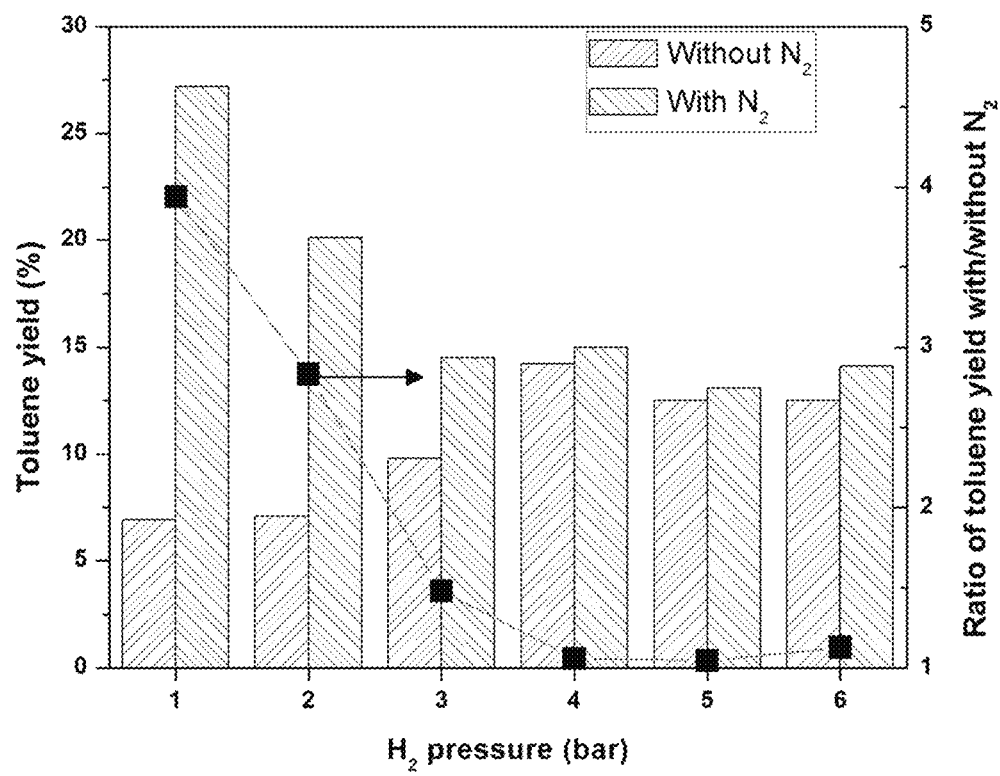

FIG. 13 shows a comparison of toluene yield at varied $H_2$ pressures. Reaction conditions: p-cresol (0.195 mmol), Ru/$TiO_2$ (25 mg), decalin (8 mL), 160° C., 1 hour, system pressure of 1-6 bar $H_2$ and 6 bar He (or 1 bar $H_2$ and 6 bar $N_2$), mixture stirred at 600 rpm.

Figure 14:
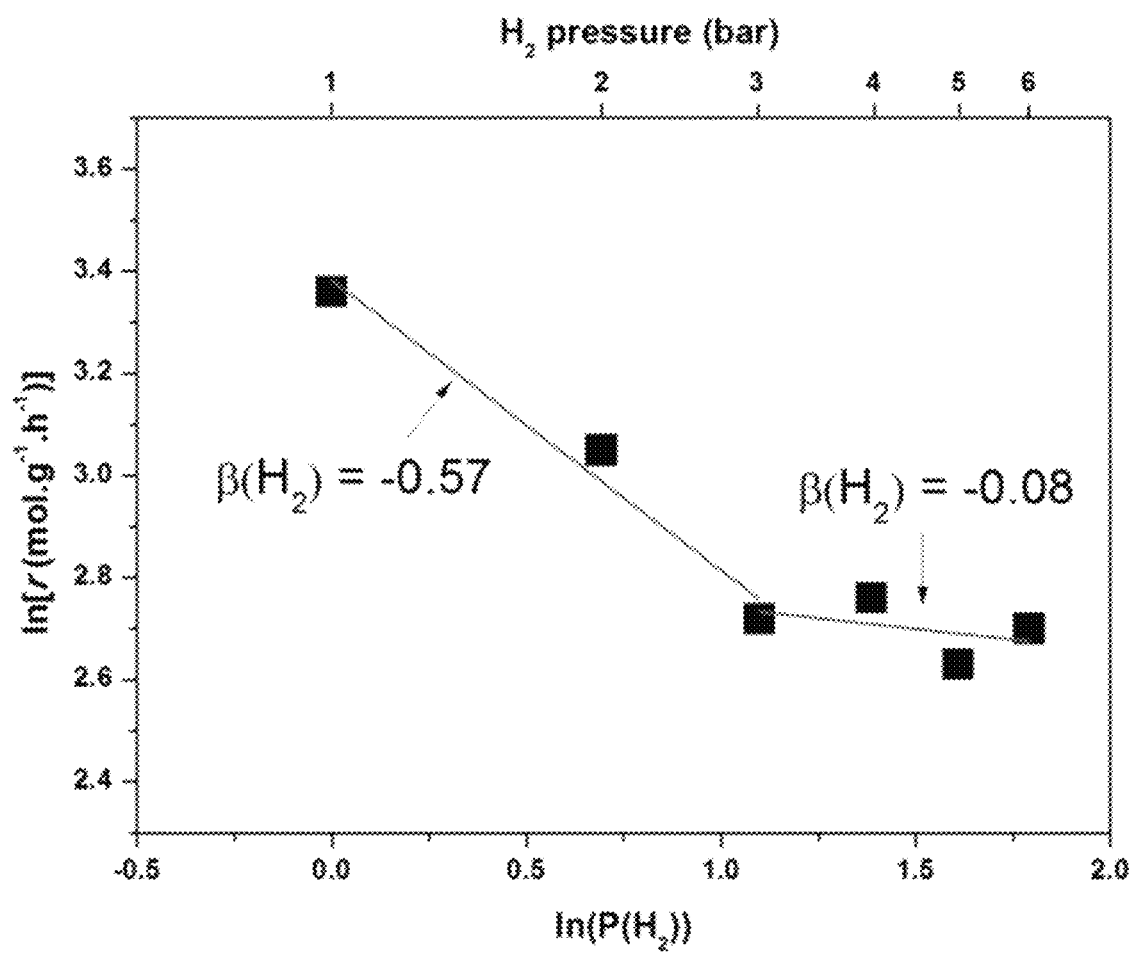

FIG. 14 shows the dependence of HDO reaction rate on the partial pressure of $H_2$ in the presence of $N_2$. The data was derived from FIG. 11b. Insert "p" represents the reaction order for $H_2$.

Figure 15:
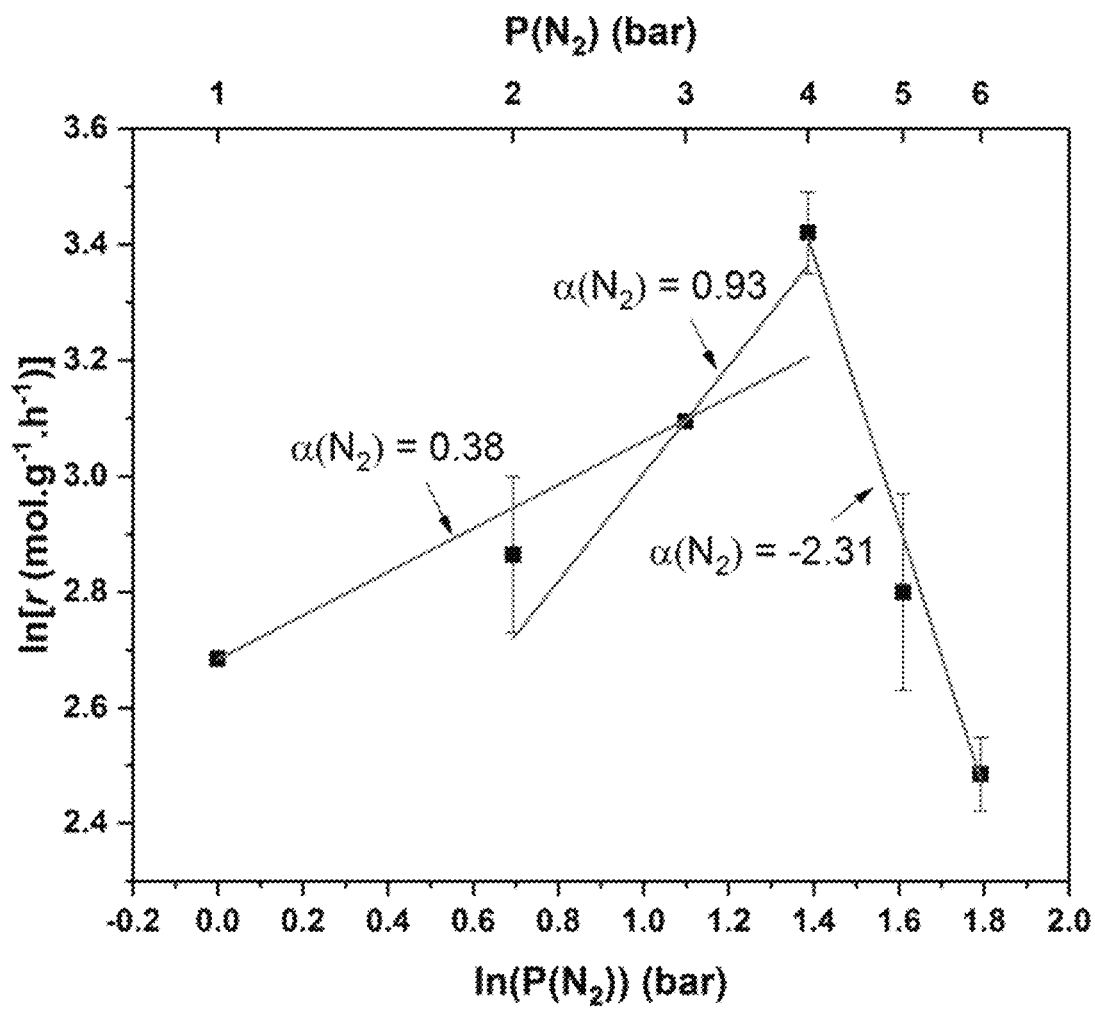

FIG. 15 shows the dependence of HDO reaction rate on the partial pressure of $N_2$. The data was derived from FIG. 11c. Inset "a" represents the reaction order for $N_2$. Error bars represent standard deviation from three independent measurements.

Figure 16:
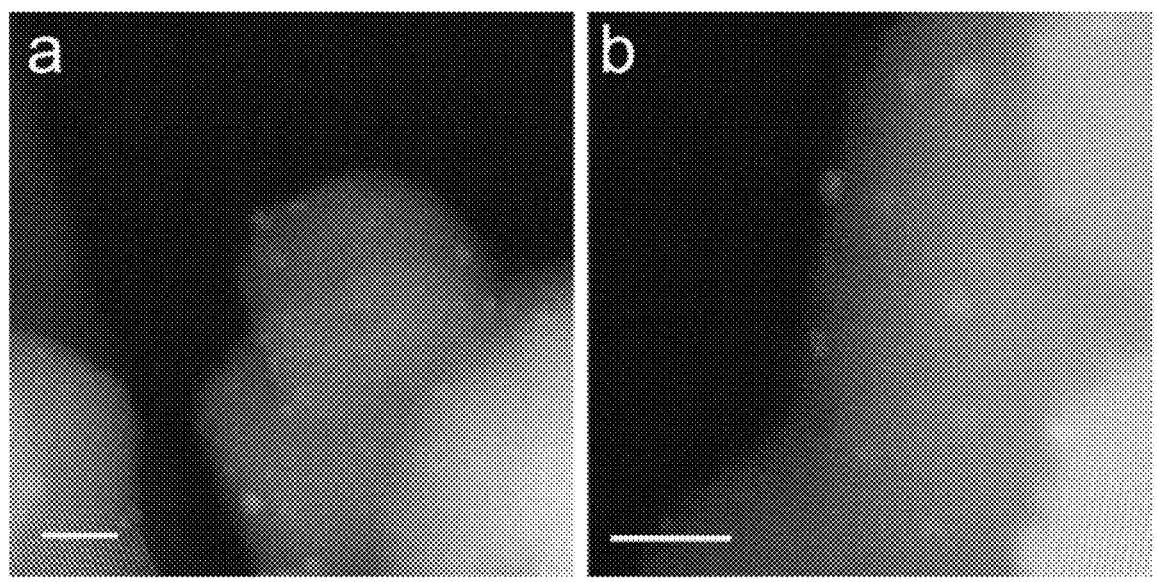

FIG. 16 shows representative HAADF images of Ru/$TiO_2$ after HDO reaction under fixed-bed conditions for 7 h. Scale bars equal 5 nm.

Figure 17:
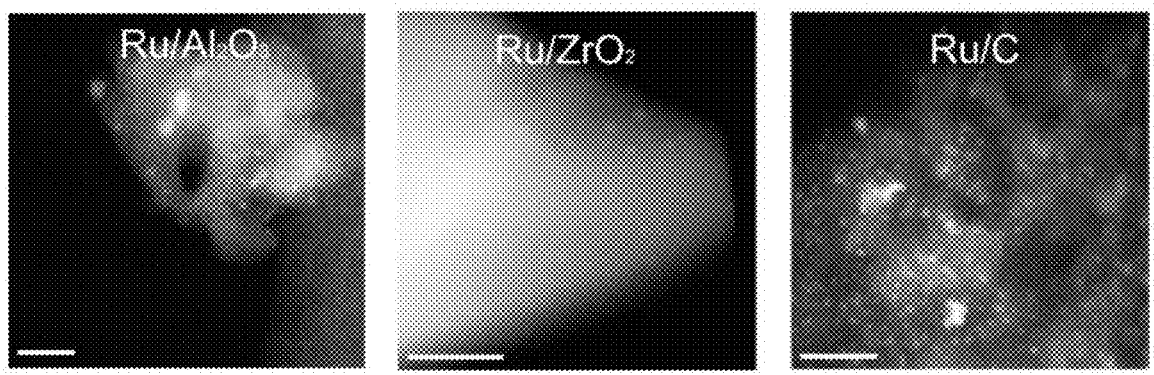

FIG. 17 shows high-angle annular dark-field scanning transmission electron microscopy images of Ru catalysts with different support. Scale bar equals 5 nm in Ru/$Al_2O_3$ image and equals 20 nm in other images.

Figure 18:
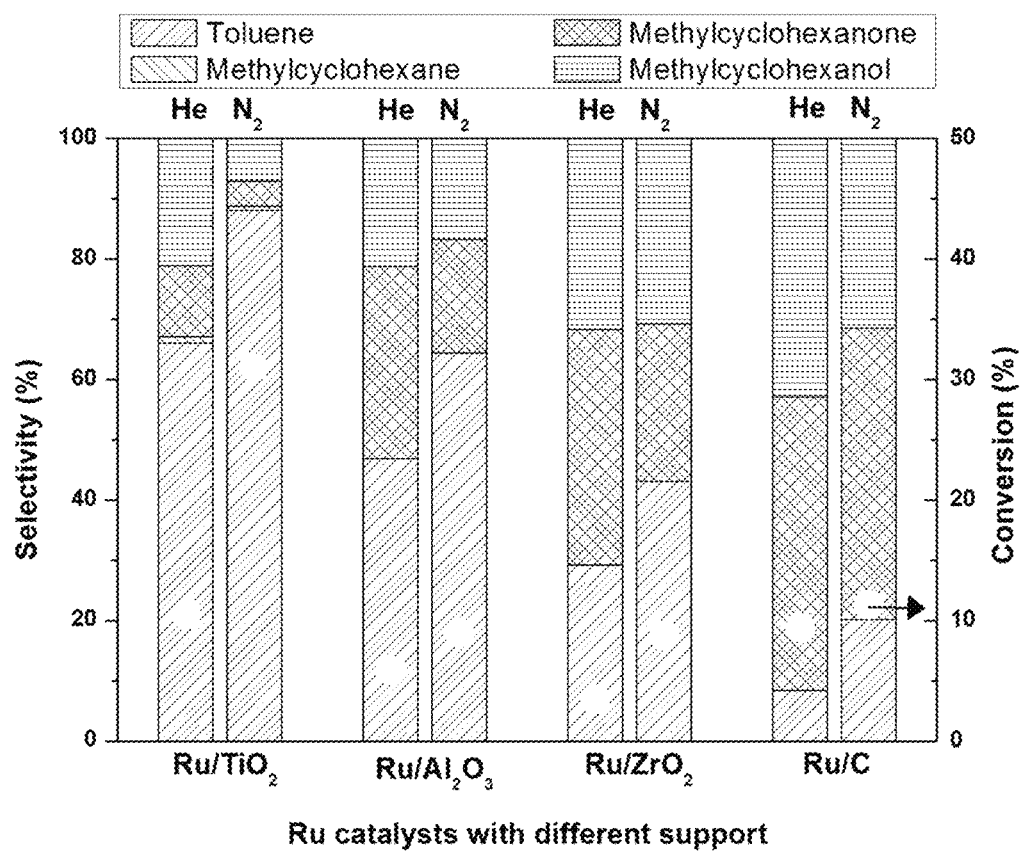

FIG. 18 shows a comparison of conversion and selectivity with/without $N_2$ in batch reaction by using Ru catalysts with different support. Reaction conditions: p-cresol (0.195 mmol), catalysts with different supports (including 0.00183 mmol Ru, which is corresponding to 25 mg for Ru/TiO$_2$, 25.5 mg for Ru/Al$_2$O$_3$, 57.4 mg for Ru/ZrO$_2$ and 3.7 mg for Ru/C), decalin (8 mL), 160° C., 1 hour, system of 1 bar H$_2$+6 bar He (or 1 bar H$_2$+6 bar N$_2$), mixture stirred at 600 rpm.

ANALYTICAL TECHNIQUES

High-Angle Annular Dark-Field Scanning Transmission Electron Microscopy (HAADF-STEM)

An aberration-corrected JEOL ARM300 CF operated at 300 kV in STEM mode was used for microstructure characterisation. The convergence angle of the probe was 26 mrad [30 μm condenser aperture] with imaging performed at 9 cm camera length. This configuration was used to collect the scattered electrons between 77 to 210 mrad (annual dark-field—ADF-signal) and 13 to 28 mrad (annular bright field—ABF-signal). Energy-dispersive X-ray elemental maps and spectra were collected using a window-less Oxford Instruments XMAX 100 TLE silicon drift detector. For STEM imaging, the probe current used was around 25 pA. The probe current was increased to around 500 pA for EDX elemental mapping.

Powder X-Ray Diffraction

Powder X-ray Diffraction (PXRD) data were obtained on a PANAnalytical X'Pert Pro diffractometer in reflection mode at 40 kV and 40 mA using Cu Kα radiation.

Gas Chromatograph-Mass Spectrometry Analysis

GC-MS and GC-FID analysis was conducted simultaneously by using an Agilent gas chromatograph equipped with an Agilent 19091 N-133 column of mode HP-INNOWax with high polarity, 30 m*250 μm*0.25 μm connected column splitter which connects to mass spectrometer and FID. The GC oven was programmed as: hold at initial temperature of 313 K for 5 minutes, ramp at 15 K minutes$^{-1}$ to 523 K and hold at 523 K for 5 minutes. The peaks were analysed by comparing the corresponding spectra with those of the NIST 2011 MS library.

Part A

Example 1—Preparation of Catalysts 1.1. Preparation of M/TiO$_2$ and M/SiO$_2$ Catalysts (M=Ru, Pt or Pd)

M/TiO$_2$ and M/SiO$_2$ catalysts were prepared as follows: an appropriate amount of M precursor was dissolved in de-ionised water, the volume of which was determined by the water adsorption volume of metal oxides. The solution was stirred for 1 h and then dropwise added to an appropriate amount of TiO$_2$ or SiO$_2$. The obtained glue-like sample was stirred for another 2 h and dried in an oven at 397 K overnight and then reduced in H$_2$, at a flow rate of 20 cm$^3$/min and a heating rate of 2 K/min to the target temperature, with the target temperature held for several hours. The sample was subsequently cooled down to room temperature and protected with N$_2$ for 1 h prior to removal from the tube reactor for catalytic testing.

1.2. Preparation of m-Ru/TiO$_2$

RuCl$_3$ (0.0063 g, 0.03 mmol), 1-ethyl-3-methylimidazolium dicyanamide (0.0045 g) were dissolved in 3 mL de-ionised water. The mixture was stirred for 1 h and then dropwise added to TiO$_2$ (0.24 g). The obtained glue-like sample was keeping stirred for another 2 h and then dried in an oven at 397 K overnight and then reduced in H$_2$, at a flow rate of 20 cm$^3$/min and a heating rate of 2 K/min to 673 K, with the target temperature held for 3 h. The sample was subsequently cooled down to room temperature and protected with N$_2$ for 1 h prior to removal from the tube reactor for catalytic reaction.

Example 2—Catalytic Testing 2.1. General Procedure

An appropriate amount of catalytic substrate (e.g. p-cresol or bio-oil), catalyst and decalin were added to a Parr reactor (reactor volume, 50 mL) and sealed. After purging the reactor with H$_2$, the reaction was carried out with an appropriate pressure of H$_2$, N$_2$ and/or He at 120° C. for 1 hour with a stirring speed of 600-800 rpm. After the reaction was completed and cooled down to room temperature, the organic mixture of the products was collected, qualitatively analyzed by GC-MS, and quantitively analysed by GC-FID.

2.2. Results and Discussion

The effect of nitrogen on the ability of various deoxygenation catalysts to catalyse the deoxygenation of p-cresol to toluene was investigated. The results are outlined in Table 1 below:

TABLE 1

Effect of nitrogen on the catalytic performance of various catalysts in the conversion of 4-methylphenol to toluene. Reactor: Parr 50 mL batch reactor. Temperature = 120° C. 8 mL decalin. Stirring speed = 600 rpm.

| Run | Cat | Mass catalyst (mg) | Mass p-cresol (mg) | P(bar) of H$_2$ | P(bar) of He | P(bar) of N$_2$ | t (h) | Conv. (%) | Toluene selec. (%) | TOF (h$^{-1}$) |
|---|---|---|---|---|---|---|---|---|---|---|
| 1 | Ru/TiO$_2$ | 10 | 21.1 | 1 | 6 | 0 | 1 | 1.8 | 54.7 | 1.6 |
| 2 | Ru/TiO$_2$ | 10 | 21.1 | 1 | 0 | 6 | 1 | 5.8 | 84.7 | 7.7 |
| 3 | m-Ru/TiO$_2$ | 10 | 21.1 | 1 | 6 | 0 | 1 | 3.4 | 55.5 | 3.0 |
| 4 | m-Ru/TiO$_2$ | 10 | 21.1 | 1 | 0 | 6 | 1 | 11.8 | 77.2 | 14.4 |
| 5 | Ru/C* | 10 | 21.1 | 1 | 6 | 0 | 1 | 38.9 | 4.3 | 0.7 |
| 6 | Ru/C* | 10 | 21.1 | 1 | 0 | 6 | 1 | 35.9 | 12.5 | 1.8 |
| 7 | Ru/SiO$_2$ | 10 | 21.1 | 1 | 6 | 0 | 1 | 0.9 | 45.4 | 0.6 |
| 8 | Ru/SiO$_2$ | 10 | 21.1 | 1 | 0 | 6 | 1 | 1.2 | 68.5 | 1.3 |
| 9 | Pd/TiO$_2$ | 10 | 21.1 | 1 | 6 | 0 | 1 | 37.7 | 6.1 | 3.6 |
| 10 | Pd/TiO$_2$ | 10 | 21.1 | 1 | 0 | 6 | 1 | 24.3 | 30.8 | 11.8 |

TABLE 1-continued

Effect of nitrogen on the catalytic performance of various catalysts in the conversion of 4-methylphenol to toluene. Reactor: Parr 50 mL batch reactor. Temperature = 120° C. 8 mL decalin. Stirring speed = 600 rpm.

| Run | Cat | Mass catalyst (mg) | Mass p-cresol (mg) | P(bar) of $H_2$ | P(bar) of He | P(bar) of $N_2$ | t (h) | Conv. (%) | Toluene selec. (%) | TOF ($h^{-1}$) |
|---|---|---|---|---|---|---|---|---|---|---|
| 11 | $Pt/TiO_2$ | 10 | 21.1 | 1 | 6 | 0 | 1 | 28.8 | 24.5 | 11.1 |
| 12 | $Pt/TiO_2$ | 10 | 21.1 | 1 | 0 | 6 | 1 | 26.1 | 45.3 | 18.7 |

*commercially-obtained 5 wt. % Ru on carbon. All ofther catalysts contained 1.25 wt. % M relative to weight of $TiO_2/SiO_2$.

Figure 1:
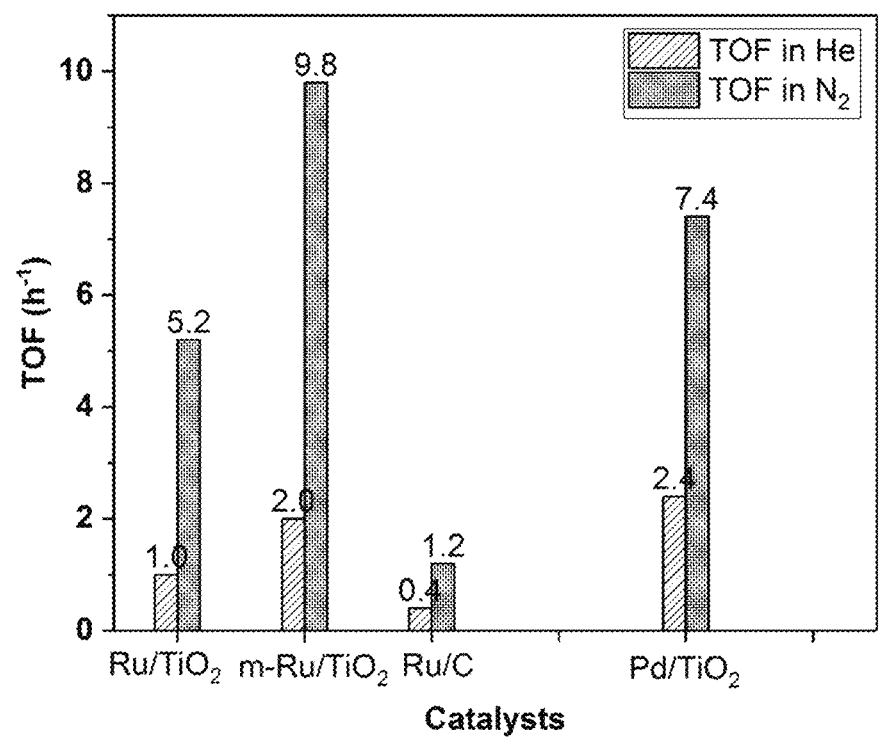
Figure 2:
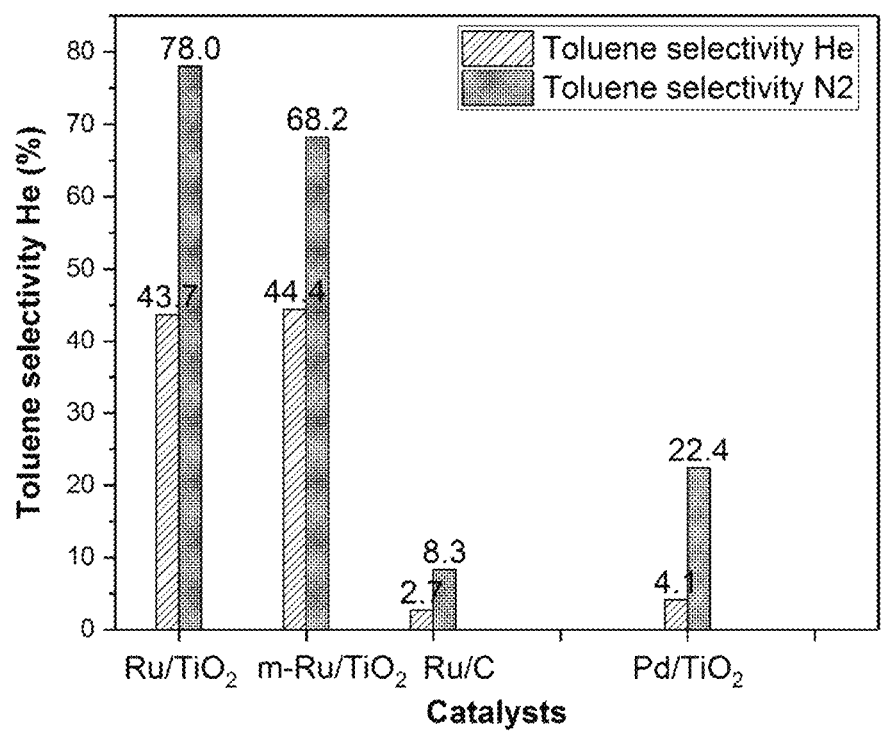

The results outlined in Table 1 illustrate that nitrogen had a beneficial effect on the activity and/or toluene selectivity of all of the catalysts tested. Similar trends are illustrated in FIGS. 1-2. It is also clear from the results that the use of nitrogen allows the catalytic process to be satisfactorily performed at a reduced temperature and/or pressure.

In order to investigate the effect of $N_2$ in the conversion of p-cresol to toluene, the catalytic activity of m-Ru/$TiO_2$ (Example 1.2) was tested at various $N_2$ pressures (with $H_2$ pressure and He pressure kept constant). The results are shown in Table 2 and FIGS. 3 to 6.

Figure 3:
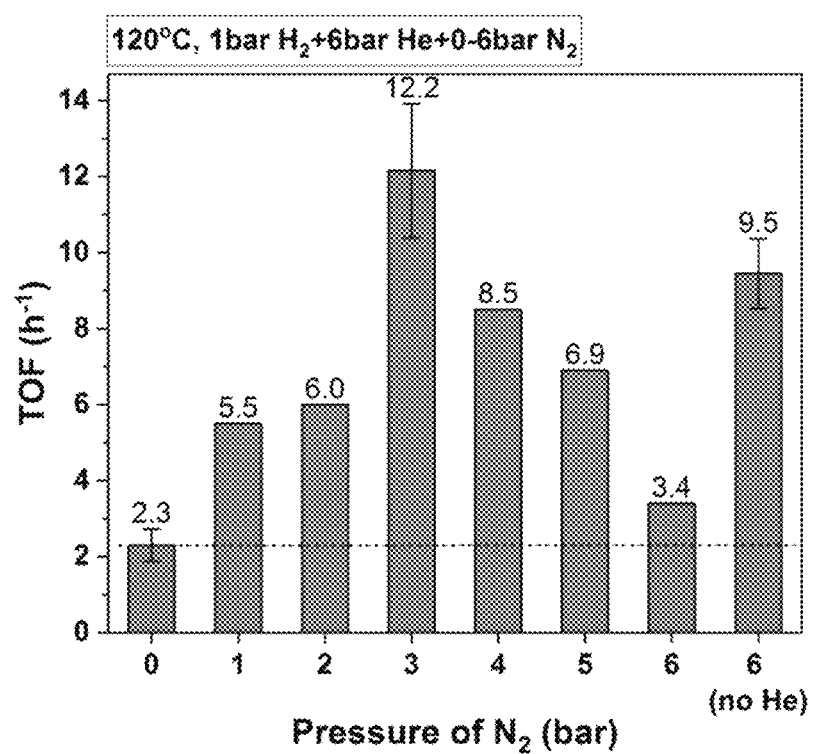
Figure 4:
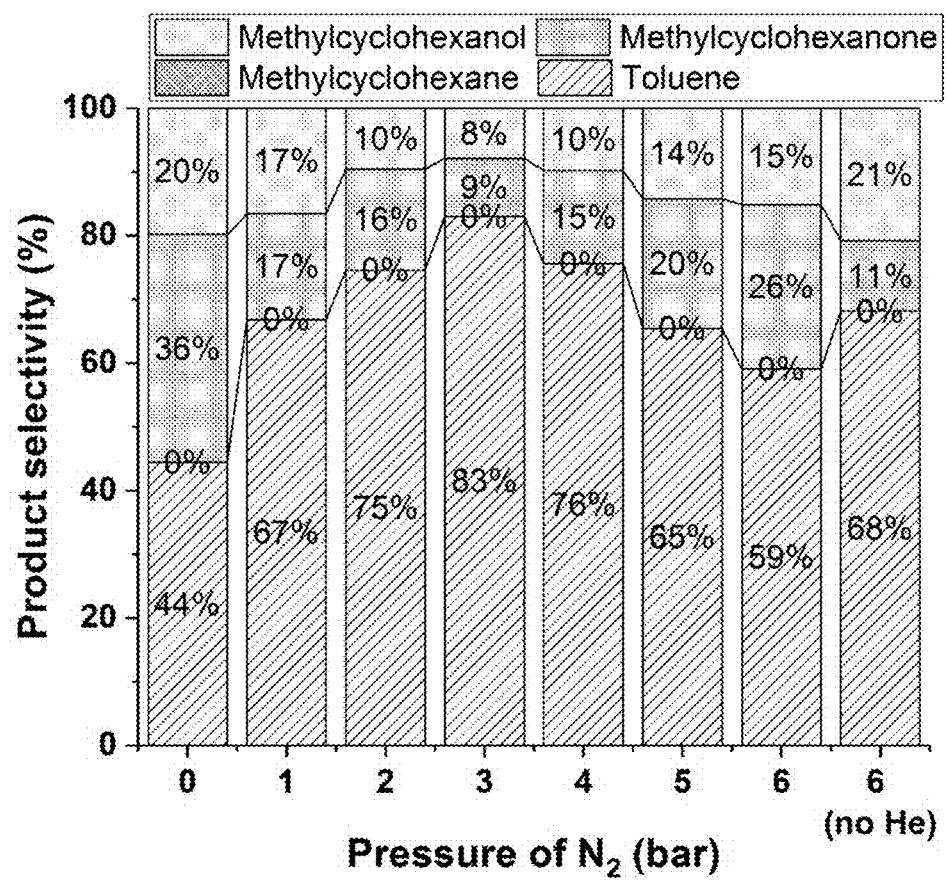
Figure 5:
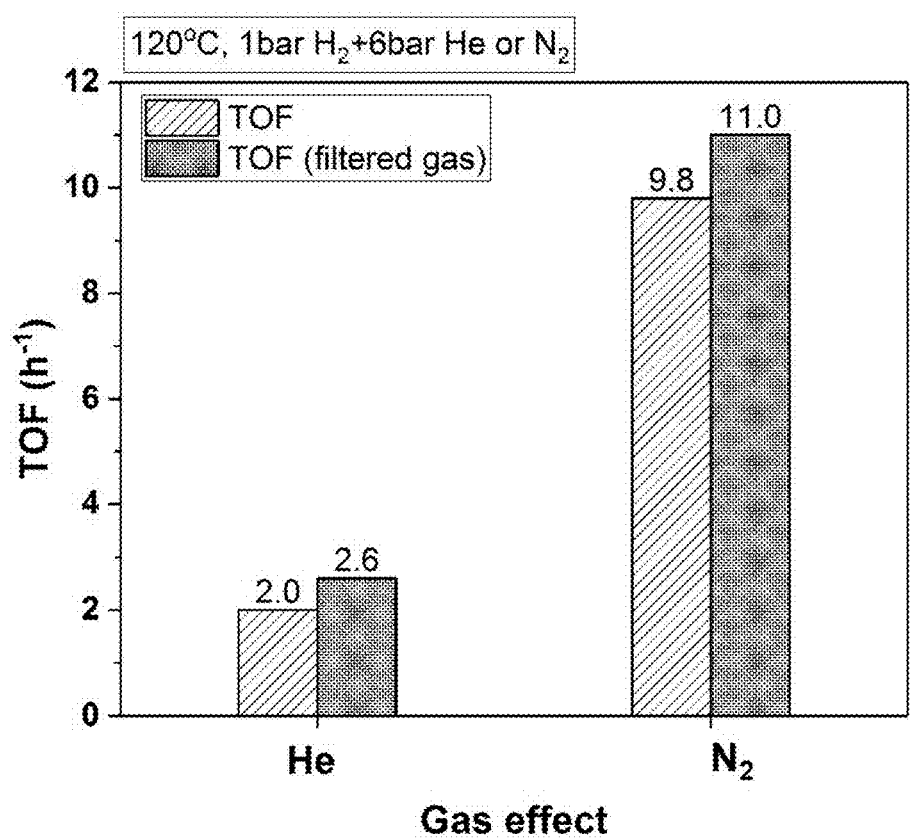
Figure 6:
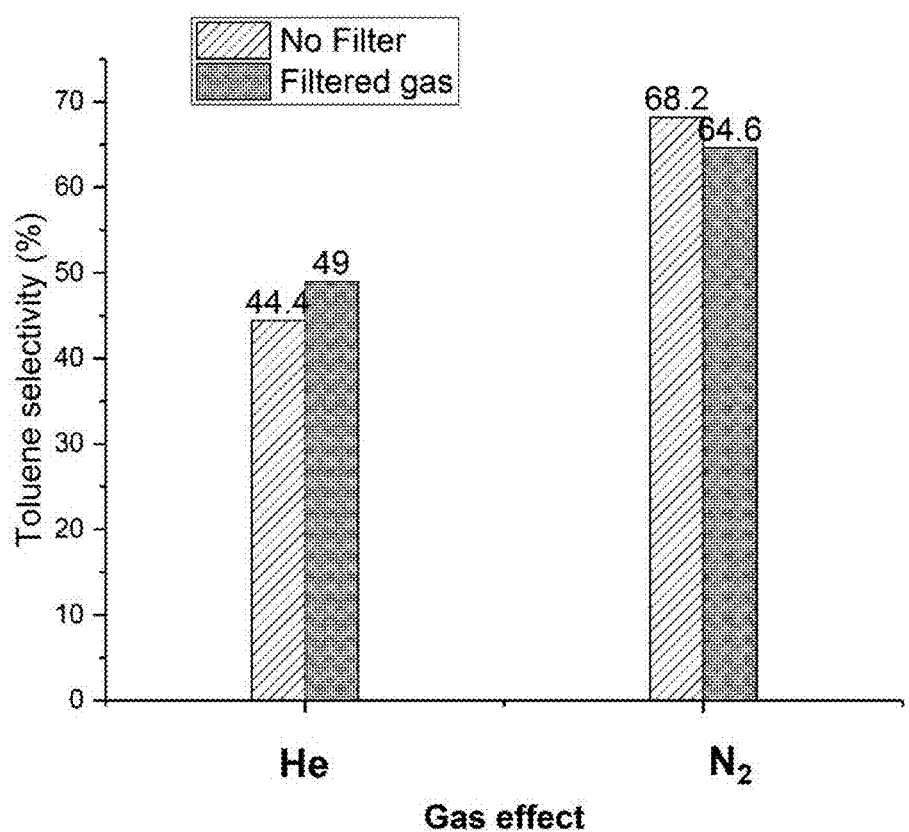

As shown in FIG. 3, the activity was more than twice as high when 1 bar $N_2$ was fed into the reaction (TOF=5.5 v.s. 2.3 $h^{-1}$). It was further increased by a factor of greater than 6 when 3 bar $N_2$ was fed (TOF=12.2 v.s. 2.3 $h^{-1}$). Further increasing $N_2$ led to higher activity compared to when no $N_2$ was present. By using 1 bar $H_2$ and 6 bar $N_2$ in the absence of He, the activity was also comparable with that of the highest obtained value (TOF=9.5 v.s. 12.2 $h^{-1}$). These results clearly show that incorporating $N_2$ gas boosts catalytic activity for deoxygenation reaction using m-Ru/$TiO_2$. FIG. 4 shows that increasing the $N_2$ pressure also has an effect on toluene selectivity. To verify the effect of $N_2$, the gases ($N_2$ and He) were filtered before purging, thereby removing any moisture and oxygen which may affect the catalytic performance. The results show only a minor difference in terms of TOF number (FIG. 5) and selectivity (FIG. 6) after the gases was

TABLE 2 catalytic performance in the conversion of 4-methylphenol to toluene by using m-Ru/$TiO_2$ catalysts at different conditions. Reactor: Parr 50 mL batch reactor.

| Entry | Catalyst | Mass catalyst (mg) | Mass p-cresol (mg) | T(° C.) | P(bar) of $H_2$ | P(bar) of He | P(bar) of $N_2$ | P(bar) of CO | t (h) | Conv. (%) | Toluene selec.(%) | TOF ($h^{-1}$) |
|---|---|---|---|---|---|---|---|---|---|---|---|---|
| 1 | m-Ru/$TiO_2$ | 12.5 | 21.1 | 240 | 1 | 6 | 0 | 0 | 1 | 64.1 | 99.2 | 80.3 |
| 2 | m-Ru/$TiO_2$ | 12.5 | 21.1 | 240 | 1 | 0 | 6 | 0 | 1 | 97.6 | 99.9 | 123.2 |
| 3 | m-Ru/$TiO_2$ | 25 | 21.1 | 180 | 1 | 0 | 6 | 0 | 1 | 94.5 | 94.9 | 56.6 |
| 4 | m-Ru/$TiO_2$ | 50 | 21.1 | 120 | 1 | 0 | 6 | 0 | 9 | 90.1 | 81.1 | 3.3 |
| 5 | m-Ru/$TiO_2$ | 50 | 21.1 | 90 | 1 | 0 | 6 | 0 | 12 | 43.1 | 30.3 | 0.3 |
| 6 | m-Ru/$TiO_2$ | 50 | 21.1 | 60 | 1 | 0 | 6 | 0 | 24 | 40.1 | 11.2 | 0.06 |
| 7 | m-Ru/$TiO_2$ | 10 | 21.1 | 120 | 1 | 6 | 0 | 0 | 1 | 3.4 | 55.5 | 3.0 |
| 8 | m-Ru/$TiO_2$ | 10 | 21.1 | 120 | 1 | 6 | 0 | 0 | 1 | 4.1 | 58.6 | 3.8 |
| 9 | m-Ru/$TiO_2$ | 10 | 21.1 | 120 | 1 | 6 | 0 | 0 | 1 | 4.1 | 60.1 | 3.9 |
| 10 | m-Ru/$TiO_2$ | 10 | 21.1 | 120 | 1 | 6 | 0 | 0 | 1 | 5.8 | 55.7 | 5.1 |
| 11 | m-Ru/$TiO_2$ | 10 | 21.1 | 120 | 1 | 0 | 6 | 0 | 1 | 11.8 | 77.2 | 14.4 |
| 12 | m-Ru/$TiO_2$ | 10 | 21.1 | 120 | 1 | 0 | 6 | 0 | 1 | 10.1 | 80.4 | 12.8 |
| 13 | m-Ru/$TiO_2$ | 10 | 21.1 | 120 | 1 | 0 | 6 | 0 | 1 | 13.8 | 74.2 | 16.2 |
| 14 | m-Ru/$TiO_2$ | 10 | 21.1 | 120 | 1 | 0 | 6 | 0 | 1 | 12.7 | 76.4 | 15.3 |
| 15 | m-Ru/$TiO_2$ | 10 | 21.1 | 120 | 1 | 0 | 0 | 6 | 1 | 0.4 | 0 | 0 |
| 16 | m-Ru/$TiO_2$ | 10 | 21.1 | 120 | 1 | 6 | 0 | 1 | 1 | 0 | 0 | 0 |
| 17 | m-Ru/$TiO_2$ | 10 | 21.1 | 120 | 1 | 0 | 6 | 1 | 1 | 0 | 0 | 0 |
| 18 | m-Ru/$TiO_2$ | 10 | 21.1 | 120 | 5 | 0 | 0 | 0 | 1 | 36.6 | 14.2 | 8.2 |
| 19 | m-Ru/$TiO_2$ | 10 | 21.1 | 120 | 5 | 0 | 0 | 0 | 1 | 38.5 | 14.6 | 8.9 |
| 20 | m-Ru/$TiO_2$ | 10 | 21.1 | 120 | 5 | 6 | 0 | 0 | 1 | 32.0 | 18.3 | 9.3 |
| 21 | m-Ru/$TiO_2$ | 10 | 21.1 | 120 | 5 | 0 | 6 | 0 | 1 | 28.9 | 18.4 | 8.4 |
| 22 | m-Ru/$TiO_2$ | 10 | 21.1 | 120 | 5 | 6 | 0 | 0 | 1 | 38.0 | 20.2 | 12.1 |
| 23 | m-Ru/$TiO_2$ | 10 | 21.1 | 120 | 5 | 6 | 0 | 0 | 1 | 36.3 | 22.6 | 13.0 |
| 24 | m-Ru/$TiO_2$ | 10 | 21.1 | 120 | 1 | 6 | 0 | 0 | 1 | 3.4 | 55.5 | 3.0 |
| 25 | m-Ru/$TiO_2$ | 10 | 21.1 | 120 | 1 | 6 | 0 | 0 | 1 | 4.1 | 58.6 | 3.8 |
| 26 | m-Ru/$TiO_2$ | 10 | 21.1 | 120 | 1 | 6 | 1 | 0 | 1 | 6.7 | 76.0 | 8.0 |
| 27 | m-Ru/$TiO_2$ | 10 | 21.1 | 120 | 1 | 6 | 2 | 0 | 1 | 6.8 | 82.1 | 8.8 |
| 28 | m-Ru/$TiO_2$ | 10 | 21.1 | 120 | 1 | 6 | 3 | 0 | 1 | 13.7 | 88.5 | 19.1 |
| 29 | m-Ru/$TiO_2$ | 10 | 21.1 | 120 | 1 | 6 | 3 | 0 | 1 | 12.1 | 81.8 | 15.7 |
| 30 | m-Ru/$TiO_2$ | 10 | 21.1 | 120 | 1 | 6 | 4 | 0 | 1 | 9.5 | 82.9 | 12.4 |
| 31 | m-Ru/$TiO_2$ | 10 | 21.1 | 120 | 1 | 6 | 5 | 0 | 1 | 8.5 | 74.8 | 10.1 |
| 32 | m-Ru/$TiO_2$ | 10 | 21.1 | 120 | 1 | 6 | 6 | 0 | 1 | 4.6 | 69.3 | 5.1 |
| 33 | m-Ru/$TiO_2$ | 10 | 21.1 | 120 | 1 | 0 | 6 | 0 | 1 | 11.8 | 77.2 | 14.4 |
| 34 | m-Ru/$TiO_2$ | 10 | 21.1 | 120 | 3 | 0 | 6 | 0 | 1 | 26.3 | 49.4 | 20.5 |
| 35 | m-Ru/$TiO_2$ | 10 | 21.1 | 120 | 5 | 0 | 6 | 0 | 1 | 32.0 | 18.3 | 9.3 |
| 36 | m-Ru/$TiO_2$ | 10 | 21.1 | 120 | 7 | 0 | 6 | 0 | 1 | 51.7 | 13.1 | 10.7 | filtered, suggesting that the increase of catalytic activity using m-Ru/TiO$_2$ was indeed due to the presence of N$_2$ gas.

Figure 7:
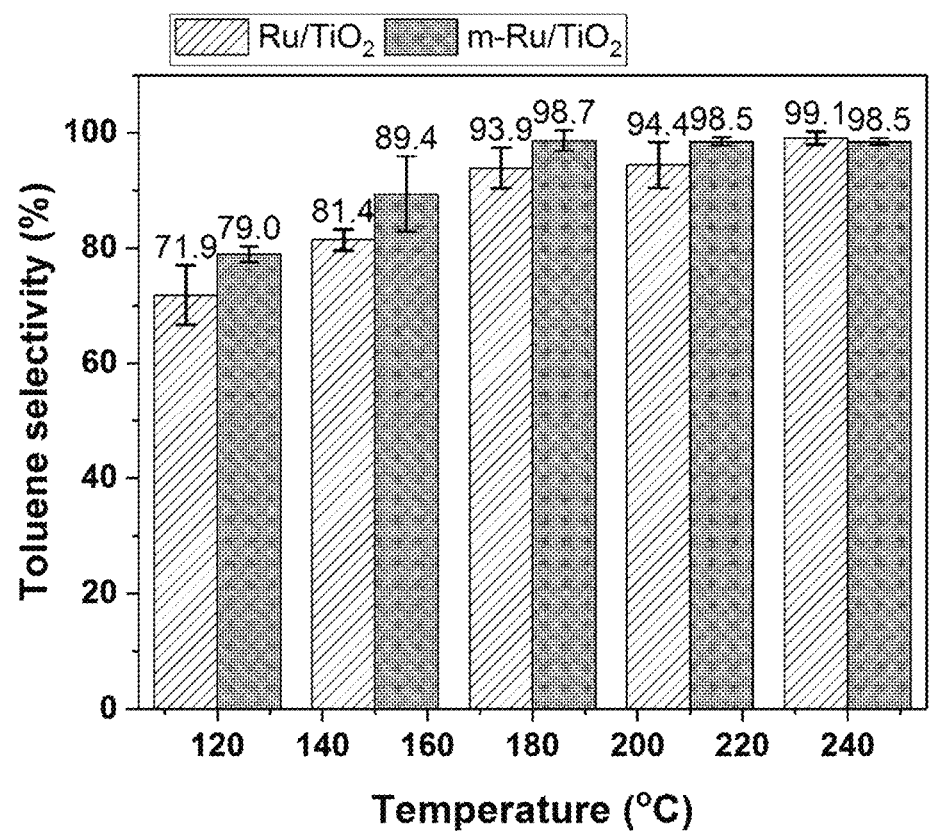
FIG. 7 shows toluene selectivity using m-Ru/$TiO_2$ and unmodified Ru/$TiO_2$ in the catalytic deoxygenation of p-cresol with varying reaction temperature. Reaction conditions: p-cresol (0.195 mmol), decalin (8 mL), 120-240° C., 1 bar $H_2$, 6 bar $N_2$, catalysts (10 mg for 60-120° C., 2.5 mg for 150-240° C.), mixture stirred at 800 rpm.

The toluene selectivity increased with increasing temperature and reached >90% when the temperature was above 180° C. (FIG. 7).

2.3. Fixed Bed Reaction

A fixed bed reaction was carried out in a HEL made continuous trickle bed reactor (mode FlowCAT) with both the liquid feed and hydrogen gas (or hydrogen gas and nitrogen gas) passing in downward direction. The Ru/TiO$_2$ catalyst (100 mg, 0.74 wt % Ru) was located in the middle of the tubular reactor with quartz wool plugs on both the sides. Liquid feed was prepared by dissolving p-cresol in decalin to form a solution of 1.12 mg/mL. The reaction was carried out at 180° C., 2 bar with H$_2$ flow rate of 10 cm$^3$(STP)minutes$^{-1}$ (or 2 bar with H$_2$ flow rate of 10 cm$^3$(STP)minutes$^{-1}$ and 6 bar with N$_2$ flow rate of 30 cm$^3$(STP)minutes$^{-1}$), and liquid flow rate of 0.2 mL minutes$^{-1}$. The liquid was preheated at the desired reaction temperature before being fed into the reactor. The products were periodically collected from the outlet stream throughout the reaction and were analysed by GC-FID. Weight hour space velocity (WHSV) was calculated by dividing the feed flow rate per hour by weight of catalyst.

Figure 8:
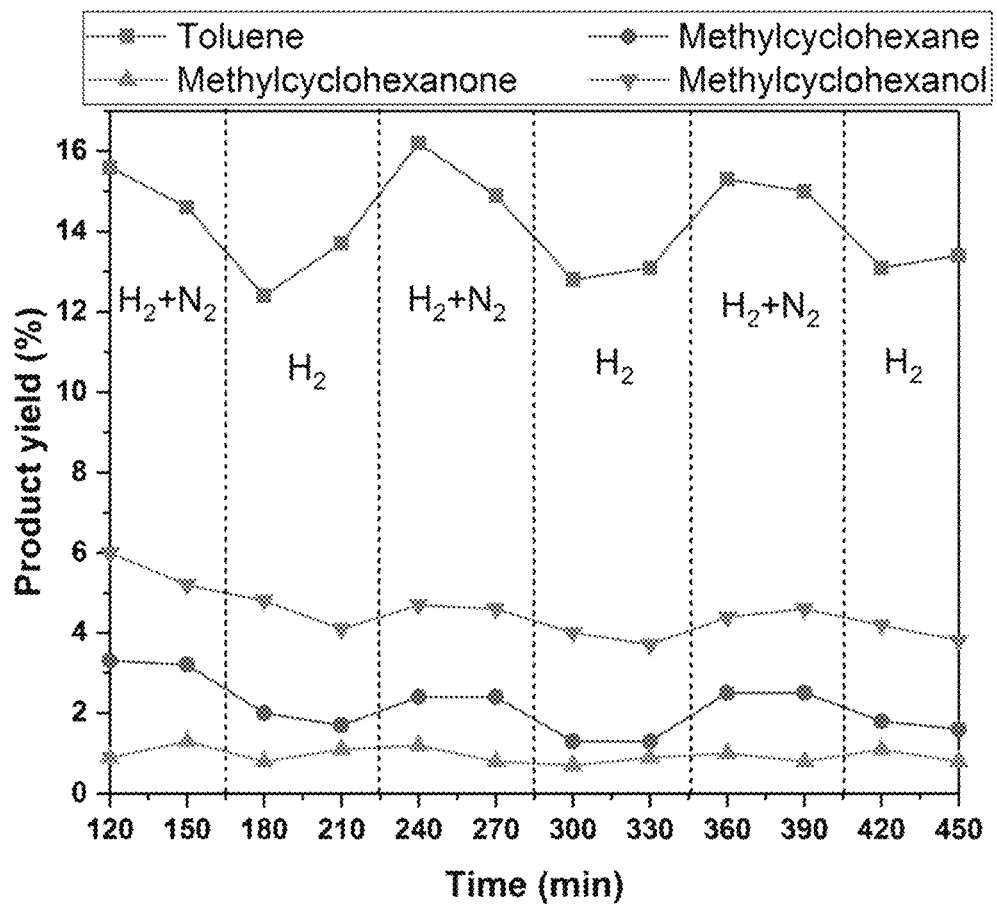
FIG. 8 shows the effect of nitrogen on product yield and toluene selectivity using Ru/$TiO_2$ in the deoxygenation of p-cresol in a fixed bed reaction.

The reaction conditions for the fixed bed reaction were as follows:
Catalyst: 100 mg Ru/TiO$_2$ (Ru: 0.74 wt %)
Temperature: 180° C.
Gas pressure: 2 bar H$_2$ or 2 bar H$_2$+6 bar N$_2$
Gas flow rate: v(H$_2$)=10 cm$^3$(STP)minutes$^{-1}$
Or v(H$_2$)=10 cm$^3$(STP)minutes$^{-1}$, v (N$_2$)=30 cm$^3$(STP)minutes$^{-1}$
Liquid concentration (p-cresol in decalin)=1.12 mg·min$^{-1}$
Liquid flow rate: 0.2 ml·min$^{-1}$
WHSV=0.134 h$^1$
The results are outlined in Table 3 and FIG. 8.

Part B

Example 3—Preparation of Catalysts

3.1. Preparation of Ru/TiO$_2$

Ru/TiO$_2$ catalyst was prepared using a wet-impregnation method. RuCl$_3$ (0.03 mmol) was dissolved in 3 mL de-ionised water. The mixture was stirred for 1 h and then added dropwise to TiO$_2$ (0.24 g). In the wet-impregnation method for preparing the catalyst, the water volume used was larger than that needed to saturate the TiO$_2$ surface, so suspension liquid rather than glue-like sample was formed. The formation of the suspension liquid allows it to be stirred vigorously for 2 hours and then the sample was dried overnight in an oven at 120° C. and then reduced in H$_2$, at a flow rate of 20 cm$^3$/min and a heating rate of 2° C./min to 400° C., with the target temperature held for 3 hours. The sample was subsequently cooled down to room temperature and protected with N$_2$ for 1 h prior to removal from the tube reactor for catalytic reactions or other tests.

3.2. Other Catalysts

Ru/Al$_2$O$_3$ and Ru/ZrO$_2$ were prepared in an analogous manner to Ru/TiO$_2$ (Example 3.1) except using the appropriate support in the place of TiO$_2$. Ru/C was purchased from Sigma-Aldrich.

Example 4—Characterisation of Ru/TiO$_2$

HAADF-STEM images revealed that Ru particles were well-dispersed on TiO$_2$ support (FIG. 9a,b and FIG. 10), with an average diameter of 1.2 nm (FIG. 9c). The composition of Ru/TiO$_2$ was shown by energy dispersive X-ray spectroscopy (EDS) analysis in a STEM mode (FIG. 9d), and the loading amount of Ru was determined to be 0.74 wt % using inductively coupled plasma mass spectrometry (ICP-AES) analysis. Powder X-ray diffractogram (PXRD) data (FIG. 9e) revealed a mixed rutile and anatase phase of TiO$_2$. There is no clear change in the reflection at 2θ=44° between TiO$_2$ and Ru/TiO$_2$ samples. The predicted Bragg reflection (201) of rutile TiO$_2$ at 2θ=44.054° coincides with the Bragg reflection (201) for Ru at 2θ=44.005° for (101).

TABLE 3

Effect of nitrogen on the catalytic performance of Ru/TiO$_2$ in the conversion of 4-methylphenol to toluene in a fixed bed reaction

| Time (min) | Gas | Conversion (%) | Yield (%) Toluene | Methylcyclohexane | Methylcyclohexanone | Methylcyclohexanol |
|---|---|---|---|---|---|---|
| 120 | H$_2$ + N$_2$ | 25.8 | 15.6 | 3.3 | 0.9 | 6 |
| 150 | H$_2$ + N$_2$ | 24.3 | 14.6 | 3.2 | 1.3 | 5.2 |
| 180 | H$_2$ | 20.0 | 12.4 | 2 | 0.8 | 4.8 |
| 210 | H$_2$ | 20.6 | 13.7 | 1.7 | 1.1 | 4.1 |
| 240 | H$_2$ + N$_2$ | 24.5 | 16.2 | 2.4 | 1.2 | 4.7 |
| 270 | H$_2$ + N$_2$ | 22.8 | 14.9 | 2.4 | 0.8 | 4.6 |
| 300 | H$_2$ | 18.9 | 12.8 | 1.3 | 0.7 | 4 |
| 330 | H$_2$ | 19.0 | 13.1 | 1.3 | 0.9 | 3.7 |
| 360 | H$_2$ + N$_2$ | 23.2 | 15.3 | 2.5 | 1 | 4.4 |
| 390 | H$_2$ + N$_2$ | 22.9 | 15 | 2.5 | 0.8 | 4.6 |
| 420 | H$_2$ | 20.2 | 13.1 | 1.8 | 1.1 | 4.2 |
| 450 | H$_2$ | 19.7 | 13.4 | 1.6 | 0.8 | 3.8 |

The results of the fixed bed reaction clearly illustrate the beneficial effect that nitrogen has on both total product yield and toluene selectivity.

Therefore, one can conclude that this reflection contains very little contribution from Ru due to the small size of the metal nanoparticles, which agrees with TEM results.

Example 5—Catalytic Performance in the Presence of $N_2$

5.1. Batch Reactor Using Ru/TiO$_2$

The catalytic performance of Ru/TiO$_2$ was evaluated for the HDO of p-cresol in a batch reactor. p-cresol (0.195 mmol) was loaded into a stainless steel Parr autoclave (reactor volume, 50 mL) with decalin (8 mL) and Ru/TiO$_2$ (2.5-50 mg). After the autoclave was sealed, it was cleaned with $N_2$ for three times, purged 6 bar $N_2$ and then 1 bar $H_2$ at room temperature. The reaction was carried out at 60-240° C. for 1-24 h with a stirring speed of 600 rpm. After the reaction was completed and cooled down to room temperature, the products were collected and was qualitatively analysed by gas chromatograph-mass spectrometry (GC-MS) and quantitatively analysed by a flame ionisation detector (GC-FID) using external standard method. The gases composition and pressure maybe changed depending on the reaction.

Table 4 shows the comparison of catalytic performance of state-of-the-art HDO catalysts and Ru/TiO$_2$ catalyst of Example 3.1 for the conversion of p-cresol or other phenols to aromatics. As comparison to HDO results from the literature[11,12,15], most Ru-based catalysts were studied at temperature higher than 200° C. (entries 1-3 in Table 4). A higher activity was observed for isolated Co atoms doped onto MoS$_2$ monolayers[10] (Co-sMoS$_2$, entry 4), but the $H_2$ pressure required was 30 bar. Although extremely mild condition was used on Ru catalysts modified by C,N-matrix (entry 5), alicyclic compounds rather than aromatics were the main products[16,17]. As seen in entry 6, the Ru/TiO$_2$ catalyst of Example 3.1 showed similar toluene selectivity under similar temperature range and lower $H_2$ pressure. Remarkably, if 6 bar $N_2$ is added to the gas mixture as the complementary gas, the conversion increased as well as toluene selectivity (entry 7).

As shown in the left columns in FIG. 11a, a 1.5-fold higher of toluene selectivity and 4.3-fold increase of HDO activity were observed in the presence of $N_2$. The promoting effect of $N_2$ in HDO reaction was also verified at another constant conversion of 21% (right two columns in FIG. 11a). Production of toluene follows a direct deoxygenation (DDO) pathway, with the formation of methylcyclohexane as over-hydrogenation product of toluene, and methylcyclohexanone and methylcyclohexanol as hydrogenation product of p-cresol (FIG. 12), which is in agreement with previous report[10].

TABLE 4

Comparison of HDO activity for the conversion of 4-methylphenol to toluene by using Ru/TiO$_2$ catalysts with/without $N_2$ and state-of-the-art HDO catalysts from literature.

| Entry | Catalyst | T (° C.) | P (bar) of $H_2$ | P (bar) of additional gas | t (h) | Conversion (%) | Toluene selectivity (%) | Ref. |
|---|---|---|---|---|---|---|---|---|
| 1 | Ru/Nb$_2$O$_5$ | 250 | 5 | — | 5 | 99.9 | 81.2 | 11 |
| 2 | Ru/Zr(SO$_4$)$_2$ | 240 | 2 | 6 (N$_2$) | 2 | 99 | 99$^a$ | 12 |
| 3 | Ru-WO$_x$/Si—Al | 220 | 10 | — | 1.5 | 100 | 83 | 15 |
| 4 | Co-$^s$MoS$_2$ | 180 | 30 | — | 8 | 97.6 | 98.4 | 10 |
| 5 | Ru/C,N-matrix | 40 | 5 | — | 2 | 95 | 0$^d$ | 16 |
| 6 | Ru/TiO$_2$ | 220 | 1 | 6 (He) | 2 | 75.5 | 95.1 | This work |
| 7 | Ru/TiO$_2$ | 220 | 1 | 6 (N$_2$) | 2 | 97.4 | 98.4 | This work |

T, temperature;
P, pressure;
t, time.
Reaction conditions: batch reaction, p-cresol (0.915 mmol), Ru/TiO$_2$ catalyst (25 mg), decalin (8 mL), reaction mixture stirred at 600 rpm.
$^a$Anisole as the substrate. Activity per mole of $^b$Mo and $^c$Co, respectively.
$^d$99% selectivity to cyclohexanol.

The promoting effect of $N_2$ for HDO was investigated under varied $H_2$ and $N_2$ pressures. With increased $H_2$ pressure, the toluene selectivity (FIG. 11b) as well as its yield (FIG. 13) promoted by $N_2$ became less pronounced. The reaction order for $H_2$ of Ru/TiO$_2$ catalyst was measured to be −0.57 in the presence of 1-3 bar $H_2$ (FIG. 14). The negative value could be attributed to hydrogen adatoms on the Ru surface via hydrogenolysis suppressed the adsorption of $N_2$ and thus inhibited the $N_2$ promoting effect, which is consistent with hydrogen poisoning effect observed in ammonia synthesis[18]. The preferential adsorption of $H_2$ was also confirmed by the observation of higher selectivity for hydrogenation products under higher $H_2$ pressure. With increased $N_2$ pressure from 0-4 bar, the conversion increased gradually and the toluene selectivity increased from 66.0 to 88.1% (FIG. 11c). It is known that the reaction order for $N_2$ is between 0.8-1.0 for ammonia synthesis over conventional Ru-loaded catalysts and is smaller for catalyst with stronger $N_2$ dissociation ability[18]. In this work, the HDO reaction order for $N_2$ was estimated in the range of 0.38-0.98 (FIG. 15), although strictly it is inappropriate to call it 'HDO reaction order' because nitrogen is not incorporated in the reaction products. This result implies that $N_2$ is activated on Ru/TiO$_2$ with the formation of active species that provide a lower activation barrier for the overall HDO reaction. Interestingly, the conversion and toluene selectivity start to decrease when the $N_2$ pressure was further increased.

5.2. Fixed-Bed Reactor Using Ru/TiO$_2$

Besides $N_2$ promotion effect in batch reaction, the $N_2$ promotion effect in a fixed-bed reaction was also investigated. The fixed bed reactions were performed on a reactor with mode of FlowCAT supplied by HEL (HEL is a company that specialises in research and pre-pilot scale chemical reactors and systems). The Ru/TiO$_2$ catalyst (100 mg) was located in the middle of the tubular reactor with quartz wool plugs on both the sides. Liquid feed (p-cresol dissolved in decalin with concentration of 1.12 mg·mL$^{-1}$) was fed by using a HPLC pump with constant flow rate of 0.2 mL·min$^{-1}$. The N$_2$ and H$_2$ mixing gases or H$_2$ gas were alternatively passed in downward direction with velocity controlled by mass-flow controllers, with the N$_2$ and H$_2$ flow rates of 10 and 30 cm$^3$(STP)minutes$^{-1}$, respectively, and total pressure of 8 bar mixing gas (2 bar H$_2$+6 bar N$_2$) or 2 bar H$_2$, respectively. The flow rates are respectively calibrated by using a soap film bubble flowmeter. Weight hourly space velocity was maintained at 0.134 h$^{-1}$. The reaction was carried out at 180° C. The products were collected and were qualitatively analysed by GC-MS and quantitatively analysed by GC-FID using external standard method.

The reaction was carried out at constant total pressure (7 bar) and constant H$_2$ partial pressures (1 bar), while the complementary gas was changed between 6 bar N$_2$ and 6 bar He for three successive cycles. As shown in FIG. 11d, a higher toluene selectivity (i.e. 1.2-fold higher for the 1$^{st}$ cycle) and conversion were observed in the presence of N$_2$, while the selectivity of other products were not significantly changed. The fixed-bed reaction results showed the efficiency of N$_2$ in promoting the HDO reaction. Although the catalytic results for batch and fixed-bed reactions are difficult to directly compare, both of the reaction systems show higher toluene selectivity in the HDO of p-cresol with N$_2$. The Ru/TiO$_2$ retained its particle size after reaction, as revealed by STEM imaging (FIG. 16).

5.3. Other Catalysts

It was investigated whether the N$_2$ promotion effect is a generalised phenomenon for a variety of Ru-based catalysts with different supports (Ru/TiO$_2$, Ru/Al$_2$O$_3$, Ru/ZrO$_2$ and Ru/C).

The weight loading of Ru in the catalysts was determined by ICP-AES analysis (0.73% for Ru/Al$_2$O$_3$ and 0.32% for Ru/ZrO$_2$). The weight loading of Ru in Ru/C is 5% according to the supplier. Ru particles were formed in nano-size regime (FIG. 17). Increase in HDO activity in the presence of N$_2$ was observed over these catalysts with varied supports (FIG. 18), in which TiO$_2$ exhibited a higher selectivity and conversion promoted by N$_2$.

5.4. Conclusion

The results outlined herein suggest that associative N$_2$ reduction through reaction with H-containing species provide N$_2$H$_x$ species which help to promote the p-cresol to toluene conversion over a series of Ru supported on various metal oxides or carbon catalysts.

The processes outlined herein represent an efficient strategy for promoting HDO activity over Ru-based catalysts by introducing N$_2$ into the HDO reaction. Experimental and theoretical calculations suggest that N$_2$ may be converted to N$_2$H$_x$ species, which provide protic hydrogen to assist hydrogenation of hydroxyl on p-cresol with lower activation energy than direct deoxygenation by H$_2$. These data indicate that N$_2$ should no longer be considered as a simple inert carrier gas.

While specific embodiments of the invention have been described herein for the purpose of reference and illustration, various modifications will be apparent to a person skilled in the art without departing from the scope of the invention as defined by the appended claims.

REFERENCES

1 Edward L. Kunkes, D. A. S., Ryan M. West, Juan Carlos Serrano-Ruiz, Christian A. Gartner, James A. Dumesic. Catalytic Conversion of Biomass to Monofunctional Hydrocarbons and Targeted Liquid-Fuel Classes. *Science* 322, 417-421 (2008).

2 Tushar P. Vispute, H. Z., Aimaro Sanna, Rui Xiao, George W. Huber. Renewable Chemical Commodity Feedstocks from Integrated Catalytic Processing of Pyrolysis Oils. *Science* 330, 1222-1227 (2010).

3 S. Czernik, a. A. V. B. Overview of Applications of Biomass Fast Pyrolysis Oil. *Energy & Fuels* 18, 590-598 (2004).

4 Dinesh Mohan, C. U. P., Jr., and Philip H. Steele. Pyrolysis of Wood/Biomass for Bio-oil: A Critical Review. *Energy & Fuels* 20, 848-889 (2006).

5 Elliott, D. C. Historical Developments in Hydroprocessing Bio-oils. *Energy & Fuels* 21, 1792-1815 (2007).

6 Zhao, C., Kou, Y., Lemonidou, A. A., Li, X. & Lercher, J. A. Highly selective catalytic conversion of phenolic bio-oil to alkanes. *Angew Chem Int Ed Engl* 48, 3987-3990, doi:10.1002/anie.200900404 (2009).

7 Yan, N., Yuan, Y., Dykeman, R., Kou, Y. & Dyson, P. J. Hydrodeoxygenation of lignin-derived phenols into alkanes by using nanoparticle catalysts combined with Bronsted acidic ionic liquids. *Angew Chem Int Ed Engl* 49, 5549-5553, doi:10.1002/anie.201001531 (2010).

8 Duan, H. et al. Hydrodeoxygenation of water-insoluble bio-oil to alkanes using a highly dispersed Pd—Mo catalyst. *Nat Commun* 8, 591, doi:10.1038/s41467-017-00596-3 (2017).

9 Furimsky, E. Catalytic hydrodeoxygenation. *Applied Catalysis A: General* 199, 147-190 (2000).

10 Liu, G. et al. MoS2 monolayer catalyst doped with isolated Co atoms for the hydrodeoxygenation reaction. *Nature Chemistry*, doi: 10.1038/nchem.2740 (2017).

11 Shao, Y. et al. Selective production of arenes via direct lignin upgrading over a niobium-based catalyst. *Nat Commun* 8, 16104, doi: 10.1038/ncomms16104 (2017).

12 Luo, Z., Wang, Y., He, M. & Zhao, C. Precise oxygen scission of lignin derived aryl ethers to quantitatively produce aromatic hydrocarbons in water. *Green Chem.* 18, 433-441, doi:10.1039/c5gc01790d (2016).

13 Omotoso, T., Boonyasuwat, S. & Crossley, S. P. Understanding the role of TiO2crystal structure on the enhanced activity and stability of Ru/TiO2catalysts for the conversion of lignin-derived oxygenates. *Green Chem.* 16, 645-652, doi:10.1039/c3gc41377b (2014).

14 Newman, C. et al. Effects of support identity and metal dispersion in supported ruthenium hydrodeoxygenation catalysts. *Applied Catalysis A: General* 477, 64-74, doi: 10.1016/j.apcata.2014.02.030 (2014).

15 Huang, Y.-B., Yan, L., Chen, M.-Y., Guo, Q.-X. & Fu, Y. Selective hydrogenolysis of phenols and phenyl ethers to arenes through direct C—O cleavage over ruthenium-tungsten bifunctional catalysts. *Green Chem.* 17, 3010-3017 (2015).

16 Cui, X., et al. Highly selective hydrogenation of arenes using nanostructured ruthenium catalysts modified with a carbon-nitrogen matrix. *Nat. Commun.* 7, 11326 (2016)

17 Li, Z., Assary, R. S., Atesin, A. C., Curtiss, L. A. & Marks, T. J. Rapid ether and alcohol C—O bond hydrogenolysis catalyzed by tandem high-valent metal triflate+ supported Pd catalysts. *J. Am. Chem. Soc.* 136, 104-107 (2014).

18 Kitano, M., et al. Ammonia synthesis using a stable electride as an electron donor and reversible hydrogen store. *Nat. Chem.* 4, 934-940 (2012).

The invention claimed is:

1. A catalytic process for reducing the oxygen content of an organic substrate, the process comprising the steps of:
   a) providing a mixture comprising:
      i. the organic substrate, wherein the organic substrate is one or more organic compounds selected from the group consisting of p-cresol, m-cresol, eugenol, guaiacol, 4-ethyl-guaiacol, 3-propyl-guaiacol, syringol, 4-methyl-syringol, 4-allyl-syringol and 1,3,5-trimethoxybenzene; and
      ii. a catalyst;
   b) contacting the mixture of step a) with a gaseous mixture comprising hydrogen gas and nitrogen gas to reduce the oxygen content of the organic substrate, wherein the volume ratio of hydrogen gas to nitrogen gas in step b) is 1:0.5 to 1:20.

2. The process according to claim 1, wherein the volume ratio of hydrogen gas to nitrogen gas is 1:0.5 to 1:10.

3. The process according to claim 1, wherein the volume ratio of hydrogen gas to nitrogen gas is 1:2.75 to 1:8.4.

4. The process according to claim 1, wherein the volume ratio of hydrogen gas to nitrogen gas is 1:3.25 to 1:6.5.

5. The process according to claim 1, wherein greater than 60 vol. % of the gaseous mixture used in step b) is composed of hydrogen and nitrogen.

6. The process according to claim 1, wherein the catalyst comprises one or more metals selected from the group consisting of Ru, Pt and Pd supported on a support material selected from the group consisting of titania, alumina, silica, zirconia and carbon.

7. The process according to claim 6, wherein the catalyst is selected from the group consisting of $Ru/TiO_2$, $Pd/TiO_2$ and Ru/C.

8. The process according to claim 7, wherein the catalyst is $Ru/TiO_2$.

9. The process according to claim 1, wherein the organic substrate is a mixture of organic compounds comprising p-cresol and one or more of m-cresol, eugenol, guaiacol, 4-ethyl-guaiacol, 3-propyl-guaiacol, syringol, 4-methyl-syringol, 4-allyl-syringol and 1,3,5-trimethoxybenzene.

10. The process according to claim 1, wherein the organic substrate is a mixture of oxygen-containing compounds derived from plant matter.

11. The process according to claim 10, wherein the mixture of oxygen-containing compounds derived from plant matter is:
    a biomass,
    a bio-oil, or
    liquid obtainable by the pyrolysis of a plant-derived material.

12. The process according to claim 1, wherein the organic substrate is pyrolised lignocellulosic biomass, which may be liquid.

13. The process according to claim 1, wherein the mixture of step a) further comprises a solvent.

14. The process according to claim 13, wherein the solvent is an organic solvent.

15. The process according to claim 1, wherein step b) is carried out at a temperature of 40-500° C.

16. The process according to claim 1, wherein step b) is carried out at a temperature of 80-220° C.

\* \* \* \* \*